(12) United States Patent
Thielen et al.

(10) Patent No.: US 6,258,062 B1
(45) Date of Patent: Jul. 10, 2001

(54) ENCLOSED CONTAINER POWER SUPPLY FOR A NEEDLELESS INJECTOR

(76) Inventors: Joseph M. Thielen, 3027 Cameron Ave. SE., Buffalo, MN (US) 55313; William J. Drasler, 4100 Dynasty Dr., Minnetonka, MN (US) 55345

( * ) Notice: Subject to any disclaimer, the term of this patent is extended or adjusted under 35 U.S.C. 154(b) by 0 days.

(21) Appl. No.: 09/257,619

(22) Filed: Feb. 25, 1999

(51) Int. Cl.[7] .................................................. A61M 37/00
(52) U.S. Cl. .......................... 604/141; 604/68; 604/212; 604/216
(58) Field of Search .................................... 604/212, 216, 604/131, 140, 141, 143, 146, 68

(56) References Cited

U.S. PATENT DOCUMENTS

| | | |
|---|---|---|
| 3,782,380 | 1/1974 | Van Der Gaast . |
| 3,802,430 * | 4/1974 | Schwebel et al. . |
| 3,805,783 | 4/1974 | Ismach . |
| 3,945,383 | 3/1976 | Bennett . |
| 4,059,107 | 11/1977 | Iriguchi . |
| 4,089,334 | 5/1978 | Schwebel . |
| 4,090,512 | 5/1978 | Doherty . |
| 4,342,310 | 8/1982 | Lindmayer . |
| 4,400,171 | 8/1983 | Dettbarn . |
| 4,421,508 | 12/1983 | Cohen . |
| 4,623,332 | 11/1986 | Lindmayer . |
| 4,626,242 | 12/1986 | Fejes . |
| 4,680,027 | 7/1987 | Parsons . |
| 4,722,728 | 2/1988 | Dixon . |
| 4,744,786 * | 5/1988 | Hooven . |
| 4,790,824 | 12/1988 | Morrow . |
| 4,850,967 | 7/1989 | Cosmai . |
| 4,874,367 | 10/1989 | Edwards . |
| 4,913,699 | 4/1990 | Parsons . |
| 4,940,460 | 7/1990 | Casey . |
| 5,024,656 | 6/1991 | Gasaway . |
| 5,064,413 | 11/1991 | McKinnon . |
| 5,073,165 | 12/1991 | Edwards . |
| 5,242,406 * | 9/1993 | Gross et al. . |
| 5,501,666 | 3/1996 | Spielberg . |
| 5,503,627 | 4/1996 | McKinnon . |
| 5,503,637 * | 4/1996 | McKinnon . |
| 5,569,189 | 10/1996 | Parsons . |
| 5,599,302 | 2/1997 | Lilley . |
| 6,045,534 * | 4/2000 | Jacobsen et al. . |

* cited by examiner

*Primary Examiner*—Anhtuan T. Nguyen
*Assistant Examiner*—Jeremy Thissell

(57) ABSTRACT

The power supply is for use with a needleless injector for injecting drug transcutaneously without a needle. The power supply includes an enclosed container that contains a working gas and that can change in volume without an active seal. The enclosed container can include a diaphragm, a bellows, or other structure that has a movable surface. The enclosed container power supply is a component of a needleless injector which has a latch means to hold the power supply in a loaded state and which has an activation means to release the latch and activate the power supply of the needleless injector to initiate drug delivery. The enclosed container power supply of the needleless injector can interface with a drug reservoir means which contains the drug to be delivered and can interface with a reset means to place the power supply in a loaded state. The drug reservoir means can be a disposable ampule or a reusable ampule. The reset means can be a remote reset mechanism or it can be a component of the needleless injector. The power supply can have two or more stages of volume and pressure change during activation. A two-stage power supply can operate with a larger first stage average pressure and a lower second stage average pressure and with a step change in pressure between stages in order to provide enhanced drug delivery to the patient.

39 Claims, 24 Drawing Sheets

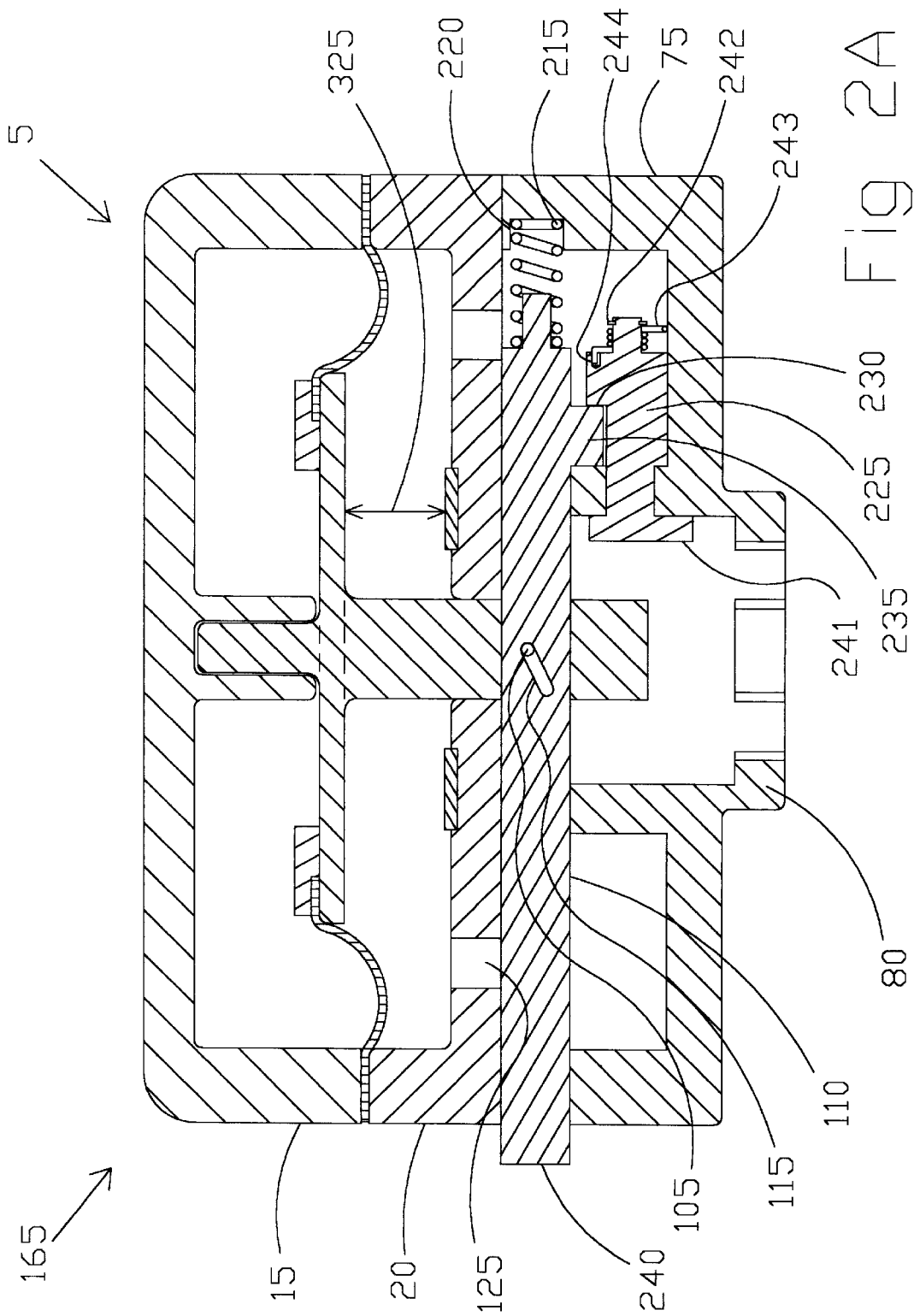

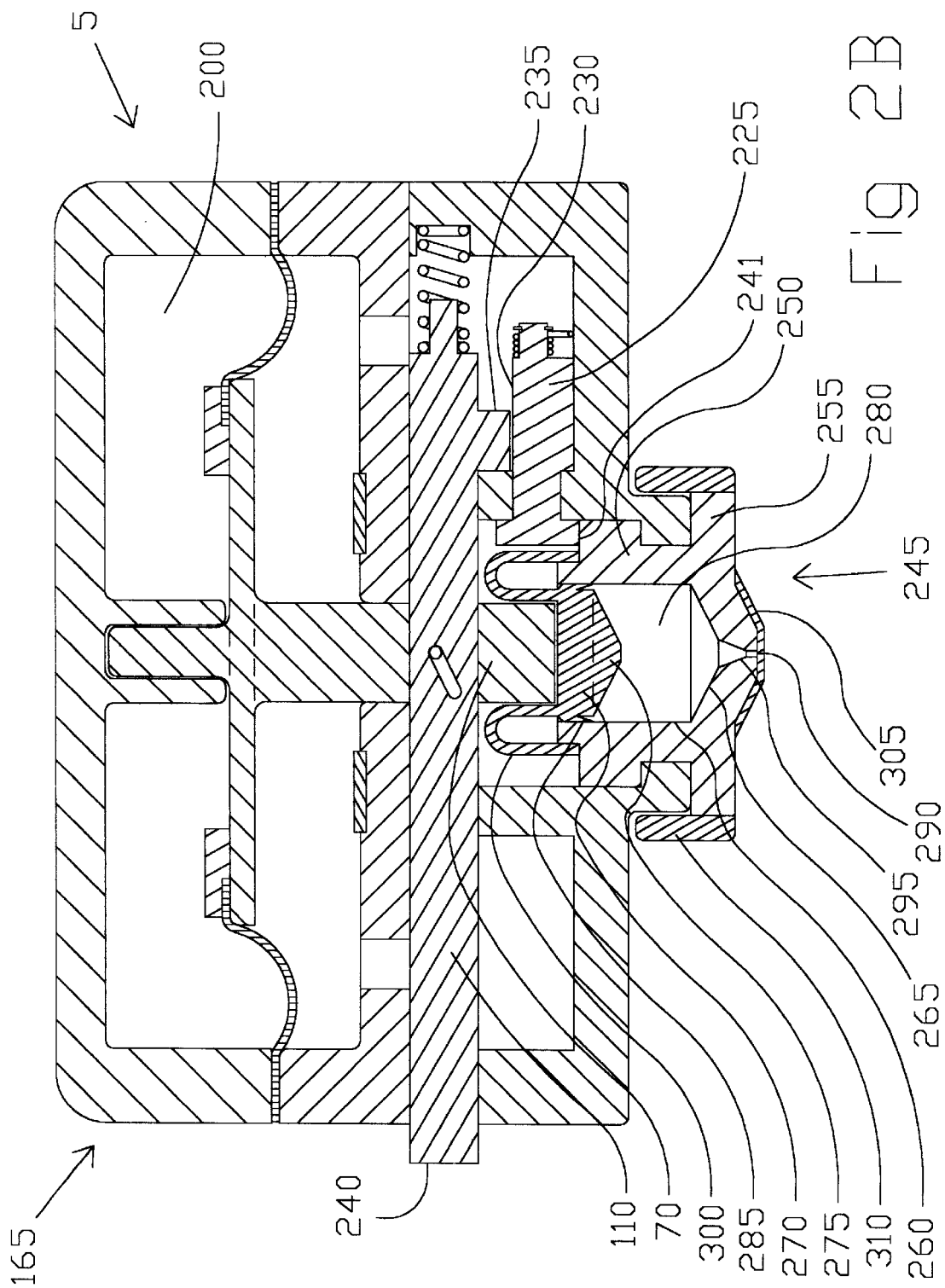

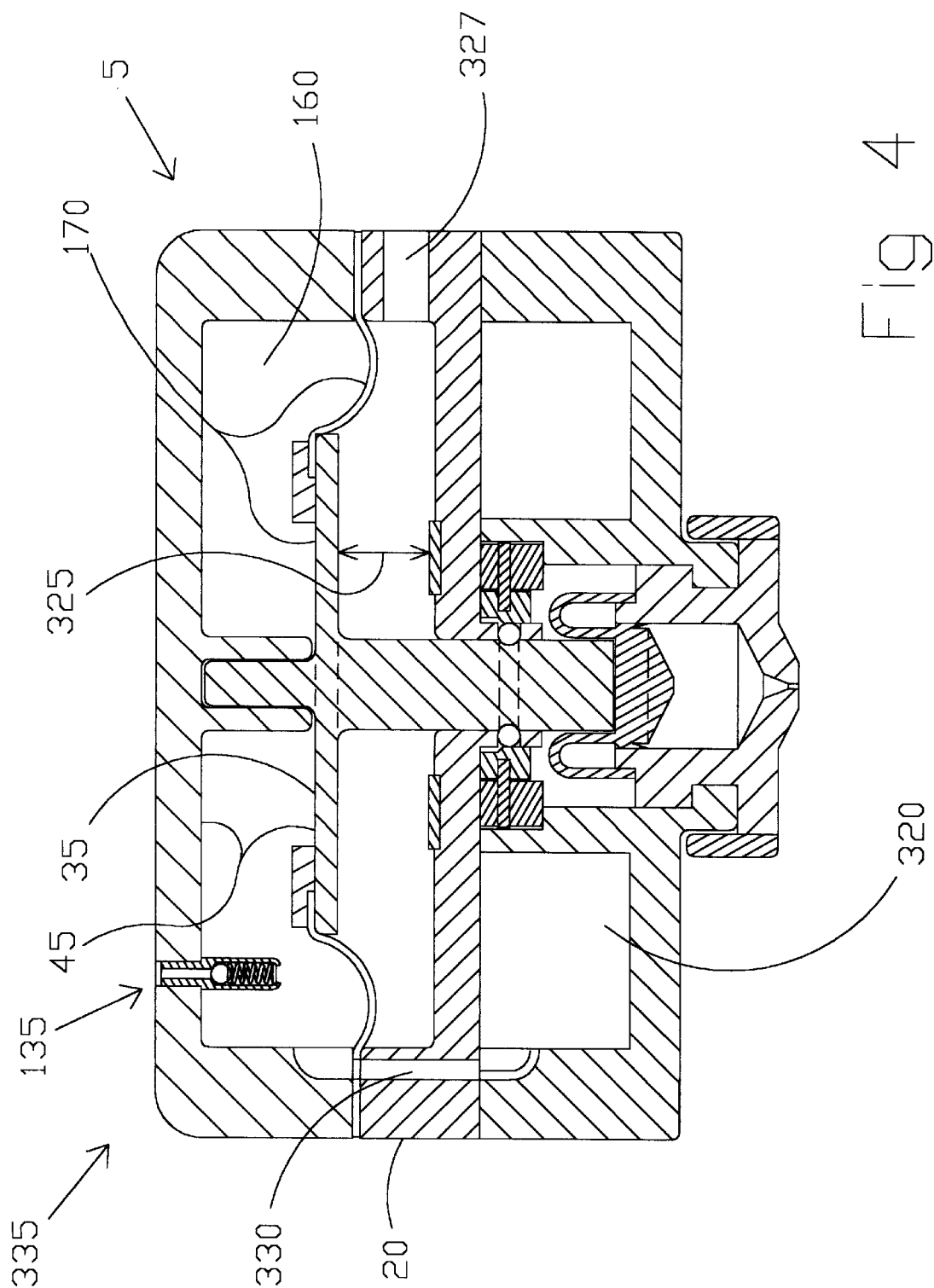

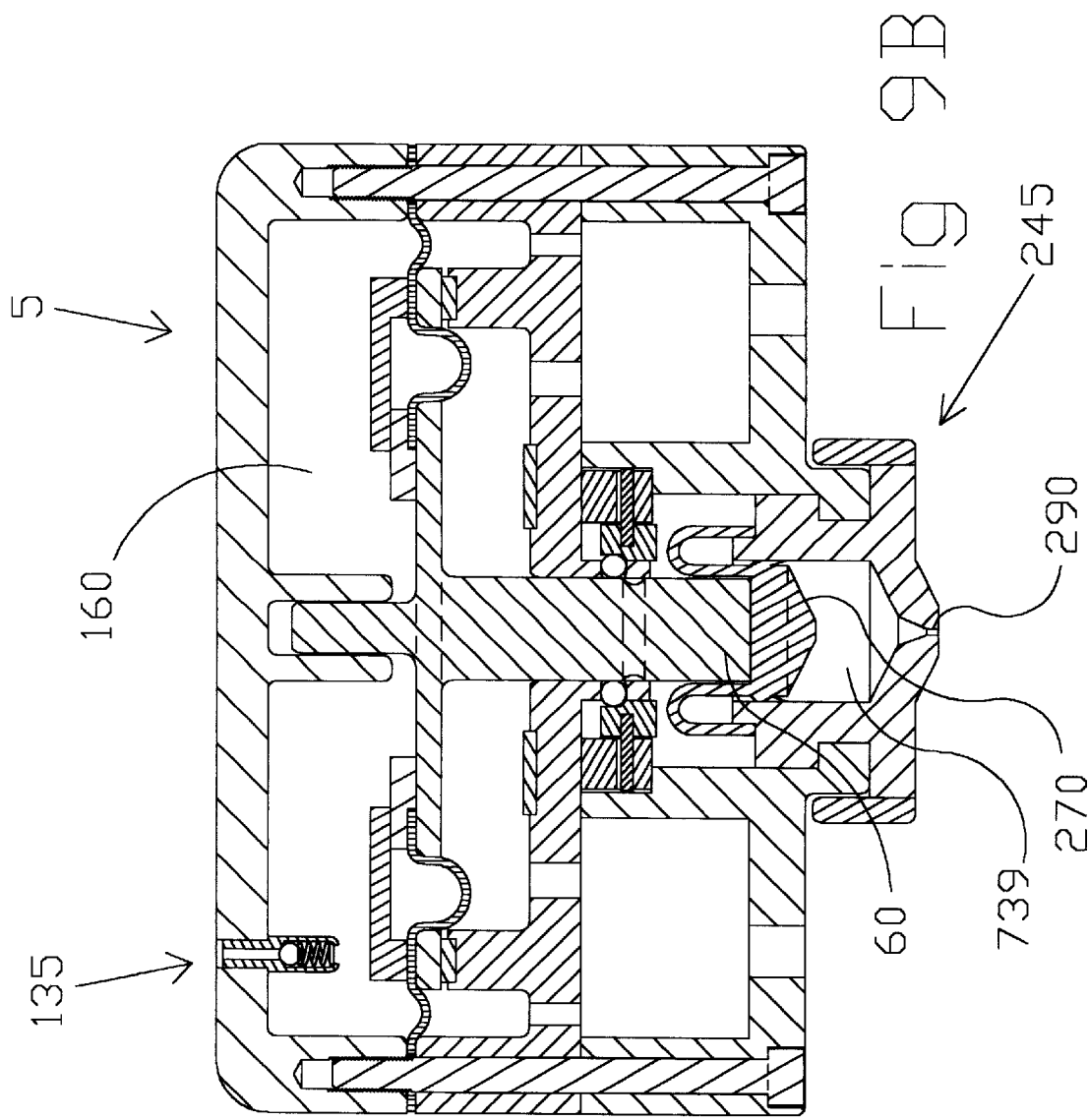

ENCLOSED CONTAINER POWER SUPPLY FOR A NEEDLELESS INJECTOR

BACKGROUND OF THE INVENTION

1. Field of Invention

The present invention relates to a power supply that can be used with most needleless injectors or other drug delivery devices for transcutaneous delivery of drugs or other rapid drug delivery. The power supply has a working gas and no active seals that can provide a leak path for the working gas out of an enclosed volume.

2. Description of Prior Art

Needleless injectors are used to inject drugs of various types transcutaneously without using a needle which is the standard modality for drug delivery. Several components that generally form a needleless injector include a power supply, a drug reservoir, and a reset mechanism. The needleless injector is usually activated from a loaded to an unloaded state by some type of trigger mechanism and is held in a loaded state prior to activation by a latch mechanism. Typically the drugs used with most needleless injectors are in a liquid or suspension form although it is possible to inject dry powder or crystalline drug transcutaneously using some needleless injector designs. The drug is usually contained in a reservoir or ampule which can take on many forms. Most ampules have a piston-like mechanism that is associated with them to apply a force onto the contained drug and force the drug out of an orifice at a high velocity and typically through the cutaneous tissue of the patient's arm. Often the piston-like mechanism of the ampule interfaces with a piston or moving surface of a power supply that generates the energy and force needed to force the drug out of the ampule orifice. The orifice found in the ampule of some needleless injectors can be positioned in contact or adjacent to the patient's skin or it can be positioned a small distance away from the skin. Some needleless injectors have a built in ampule that is not removable and can be reused. This type of design may provide a lower overall cost of use but can require cleaning and sterilization by the patient on a regular basis. Other needleless injectors are made with a built in ampule that can be removed either between injections or after several injections for purposes of cleaning or filling the ampule. In this design only the ampule need be disassembled, cleaned, and sterilized on a regular basis. Still other needleless injectors have a place or compartment for a disposable ampule which can be a one-time-use ampule that is provided to the patient in a fully contained state. This design provides the patient with an easy to use, easy to maintain system but may be more costly to provide individually packaged disposable drug doses. Some drugs are not able to withstand individual packaging in a disposable ampule due to material considerations. Other drugs can require such individualized doses for each patient that prepackaging the drug in a separate ampule may be impractical. Some needleless injectors provide for a syringe type of ampule that can be filled by the patient in a manner similarly to a standard syringe. Several problems can arise from this type of ampule system including leakage and lack of control of dose volume. Needleless injectors have advantages over conventional needle injection due to their less invasive nature, the psychological advantage of not inserting a needle through the skin, and other potential advantages including less pain and better sterility control. The present invention is a power supply that can be used with almost all needleless injectors regardless of the type of drug reservoir or ampule they have and regardless of the type of drug reservoir they may interface with.

A needleless injector has a power supply that provides the energy to drive the drug out of the orifice of the ampule. Many different types of power supplies are used with needleless injectors. Mechanical springs including disk springs and coil springs can be compressed to store potential energy that is later released to drive a liquid or dry powder drug transcutaneously into a patients body without the use of a needle. Such springs can be modified to provide spring rates and spring constants that will provide a comfortable and effective delivery of the drug into the patients tissue. Other power supplies include compressed gas cylinders and pistons that compress a gas and store potential energy in the compressed gas; this energy is stored and returned to drive the drug with a high velocity through an orifice into the patient. An additional power supply for needleless injectors include a disposable carbon dioxide liquid-gas cylinder that converts a liquid carbon dioxide into a high pressure carbon dioxide gas that is used to supply the energy to drive the drug through an orifice at high velocity; disposable liquid-gas cylinder power supply systems other than the carbon dioxide power supply could also be used with a needleless injector. The present invention is a power supply that can be used to replace the power supplies of other needleless injector designs including mechanical springs, compressed gas, and disposable liquid-gas systems. Components from other needleless injector patent designs can interface with the power supply of the present invention to provide a more efficient needleless injector device.

The needleless injectors with spring and compressed gas power supplies are generally equipped with or interface with a reset mechanism to restore the power supply to its compressed state such that the needleless injector can be used again for another needleless drug delivery. Some reset mechanisms that are included as a part of the needleless injector include screw thread, hydraulic, lever arm, and the use of compressed gas. Other needleless injectors can be reset using a table top reset unit of a mechanical, electromechanical, or hydraulic nature, or can interface with a hard surface for reset purposes. Some carbon dioxide power supplies can be reset by interfacing with a household item such as a pencil or can be reset with a spring. The power supply of the present invention can interface with a screw thread, hydraulic, lever arm, compressed gas, a table top reset unit, or other reset mechanisms that are presented in most other needleless injector patents. Several other power supply devices include pyrotechnic devices, use of carbonic acid, and special gasses that can convert back and forth between a liquid and a gas in going from a compressed state to an unloaded or fired state.

Lindmayer disclosed in U.S. Pat. No. 4,623,332 a needleless injector that uses disk springs as a power supply to drive a piston forward and deliver liquid medicine from a medicine chamber and out of an orifice. A latch is used to hold the piston in a state of potential energy and a trigger is pressed to release the latch and discharge the medicine. A threaded mechanism is used to reset the coil spring for the next injection. This device is large and heavy due to the requirements placed on the springs to provide a large force in order to generate a high velocity stream out of the orifice. It is desired for the patient to be able to carry a needleless injector unobtrusively with himself such that drug injections can be made throughout the day if necessary. It is therefore desirable to have a more powerful power supply that is smaller and lighter. The power supply of the present invention could be adapted to work with the needleless injector of Lindmayer as well as with other needleless injectors as further discussed.

Several needleless injector devices disclose the use of one or more coil springs in the power supply to generate the energy needed to drive a liquid drug out of an orifice, including U.S. Pat. No. 4,722,728 by Dixon, U.S. Pat. No. 4,850,967 by Cosmai, U.S. Pat. No. 5,569,189 by Parsons, U.S. Pat. No. 3,805,783 by Ismach, U.S. Pat. No. 4,059,107 by Iriguchi, U.S. Pat. No. 4,400,171 by Dettbarn, U.S. Pat. No. 3,782,380 by Van Der Gaast, U.S. Pat. No. 5,501,666 by Spielberg, and U.S. Pat. No. 4,874,367 by Edwards. Problems with most coil springs when used as a power source include the characteristic that compressed springs quickly become weak as they begin to expand in length. In order to generate the forces needed to drive the liquid drug out through the orifice at a high velocity requires that a coil spring have a large spring constant and have a long length. As a result the needleless injector devices with coil springs tend to be larger and heavier than desired. These disclosures describe a variety of mechanism used to reset the coil spring power supply following activation to prepare it for a subsequent activation. The disclosures also use a variety of ampule types. Dixon (U.S. Pat. No. 4,722,728) and Cosmai (U.S. Pat. No. 4,850,967) disclose a screw thread mechanism to be used to reset the coil spring power supplies of their inventions; they each describe a reusable ampule that can be used with their needleless injectors.

Parsons (U.S. Pat. No. 5,569,189) describes a table top resetting fixture with a toggle clamp design that interfaces with the needleless injector of his disclosure to reset his coil spring powered needleless injector; he discloses an ampule that is reusable and looks very similar to a syringe. Ismach (U.S. Pat. No. 3,805,783) describes a coil spring powered power supply with a hydraulic reset built into the handle; he shows a removable medicament container or vile with a supply for containing the drug and a nonremovable muzzle or ampule. Iriguchi (U.S. Pat. No. 4,059,107) and Dettbarn (U.S. Pat. No. 4,400,171) each disclose a needleless injector with a compressed gas reset and a reusable ampule. Van Der Gaast (U.S. Pat. No. 3,782,380) and Spielberg (U.S. Pat. No. 5,501,666) each disclose the use of a mechanical lever to reset the coil spring power supplies in each of their devices. Van Der Gaast (U.S. Pat. No. 3,782,380) describes a detachable medicament cartridge and Spielberg (U.S. Pat. No. 5,501,666) describes an ampule or discharge chamber that is built into the needleless injector device. Edwards (U.S. Pat. No. 4,874,367) describes a reset mechanism that requires the needleless injector to be pushed against a hard surface for reset, this procedure can be dangerous; the ampule is a sterilized cartridge that is removable and can be reused. The power supply of the present invention can be used with any of the needleless injector devices disclosed in the patents listed above as well as the patents referenced by the above listed patents.

Another type of power supply is the gas spring wherein a compressed gas contained in a cylinder expands to drive a piston to supply the energy to drive the drug transcutaneously in a patient. This power supply offers the advantage of a smaller and light weight power supply that can store more potential energy per system size and weight than a mechanical spring power supply. One problem with this power supply system is that leakage of the compressed gas from the seal that separates the piston from the cylinder. This leads to eventual loss of function of the gas spring over time and with frequency of use. Additionally, gas spring costs can be higher than other power supply systems including mechanical springs and others.

One gas spring power supply for a needleless injector is disclosed in U.S. Pat. No. 5,599,302 by Lilley. In this design the air cylinder has a rod coming out of each end and as a result it has two sliding or active seals. This design is particularly prone to gas leakage due to the presence of two active seals. This device has a built in ampule that is removable for cleaning and has a threaded mechanism to reset the gas spring. Another needleless injector device that uses compressed gas as the power supply is described by Cohen in U.S. Pat. No. 4,421,508. Cohen describes a special ampule with a tube around it and is put under vacuum to hold the skin tight against the orifice when the needleless injector is fired or activated in order to get better penetration of the drug through the skin and into the underlying tissues. The same argument is made by Morrow (U.S. Pat. No. 4,790,824) as rationale for providing a space between the orifice and the skin. The device uses a vacuum to reset the power supply and has a reusable ampule.

Another power supply uses a carbon dioxide cylinder filled with carbon dioxide liquid as a supply of compressed carbon dioxide gas for driving a medicine or drug transcutaneously with a needleless injector. Problems with this type of power supply system include the difficulty with maintaining a constant pressure needed in order to control the dose that is delivered. In addition several disclosures show one or more sliding seals that can leak over time. Casey in U.S. Pat. No. 4,940,460, McKinnon in U.S. Pat. No. 5,503,627 and Morrow in U.S. Pat. No. 4,790,824 describe carbon dioxide compressed gas power supply systems. Casey (U.S. Pat. No. 4,940,460) and McKinnon (U.S. Pat. No. 5,503,627) disclose the use of a mechanical spring to reset the power supply and Morrow (U.S. Pat. No. 4,790,824) describes the use of a pencil to reset the carbon dioxide power supply. McKinnon (U.S. Pat. No. 5,503,627) describes a detachable reusable ampule with a lure fitting for filling and Morrow (U.S. Pat. No. 4,790,824) describes a reusable or a disposable ampule. Parsons discloses in U.S. Pat. No. 4,913,699 a carbon dioxide compressed gas power supply where carbon dioxide gas is contained in a glass container which is broken to release the gas. The ampule of this device is built into the needleless injector and the reset is hydraulically activated by the medicant being used. Lindmayer discloses in U.S. Pat. No. 4,342,310 a compressed gas power supply system that uses a special gas that converts from a liquid under pressure to a gas during the expansion or power portion of the cycle. This device has three active or sliding seals that are likely to leak over time and with frequency of use. A hydraulic pump is used to reset the power supply and it is designed to work with a reusable ampule. The power supply of the present invention can be used as a power supply in any of the needleless injectors mentioned above that use a compressed gas power supply that functions as a gas spring or in the needleless injectors that have carbon dioxide cylinders to supply compressed carbon dioxide gas as the power supply. The present power supply can interface with any of the reset mechanisms or can be compatible with any type of ampule described in the above referenced patents. The power supply of the present invention can also be used as a power supply in the patents that are referenced by the above mentioned patents.

Needleless injectors with varying types of power supplies are found to be compatible with a variety of ampule designs. Gasaway describes in U.S. Pat. No. 5,024,656 describes a carbon dioxide powered needleless injector that uses a reusable ampule that looks like a syringe. This device comes with an adapter for filling the syringe. McKinnon describes in U.S. Pat. No. 5,064,413 a carbon dioxide powered needleless injector that uses a built in but removable ampule. A disposable ampule design is described in U.S. Pat. No.

3,945,383 by Bennett; this ampule is designed to interface directly with a needleless injector. Parsons (U.S. Pat. No. 4,680,027) and Edwards (U.S. Pat. No. 5,073,165) each describe disposable ampules that are compatible with their own needleless injector designs. The power supply of the present invention can be compatible with needleless injector designs regardless of the type of ampule that is used with the system.

Doherty describes in U.S. Pat. No. 4,090,512 a remote mechanism that is used for resetting a needleless injector. Although the remote mechanism is described as being used with a coil spring powered injector, it could be used to reset almost any power supply. The power supply of the present invention could similarly be used with the Doherty device or with any of the reset devices that are a component of or that interface with the needleless injectors that have been referenced above.

Two additional patents are presented which discuss alternate power supply designs. In U.S. Pat. No. 4,089,334 by Schwebel a pyrotechnically powered needleless injector is presented. This type of power supply is dangerous, loud, and is not reproducible in generating a control force to drive a drug injection. Although the power supply is quite different from the power supplies presented in the prior art patents presented above, the Schwebel needleless injector device has a disposable ampule that is very similar to those that have been presented in the references above. Fejes discloses in U.S. Pat. No. 4,626,242 a needleless injector that is powered by carbonic acid gas. This needleless injector device has a mechanical spring to perform the reset of the power supply and it is designed for use with a reusable ampule. The reset mechanism and the ampule are very similar to those of other needleless injector devices presented in the prior art references listed above. The power supply of the present invention could be combined with components of either the Schwebel (U.S. Pat. No. 4,089, 334) or the Fejes (U.S. Pat. No. 4,626,242) device to form a functional needleless injector device.

SUMMARY OF THE INVENTION

The present invention overcomes the disadvantages of power supplies used in other prior art needleless injectors. The power supply of the present invention includes an enclosed container that contains a working gas such as nitrogen, carbon dioxide, or another gas. The power supply of the present invention is intended to be used with a needleless injector for transcutaneous delivery of a high velocity stream of drug from a drug ampule to a patient without the use of a needle. The enclosed container is capable of changing in volume due to the presence of a movable surface which is a component of or is attached to a flexible diaphragm, a flexible bellows, or another flexible volume container element or component. The movable surface can interface with a reset mechanism in order to reduce its volume to an initial smaller volume thereby compressing the working gas, storing potential energy, and placing the power supply and the needleless injector in a loaded state. The power supply is held in the loaded state by a latch means. The latch means can be external to the power supply and can be a component of the needleless injector. The stored energy can then be released by activating an activation means allowing the compressed working gas to expand causing the movable surface to move allowing the enclosed container and the needleless injector to achieve an unloaded state. The movable surface interfaces with a drug ampule to deliver the drug from the ampule transcutaneously into the patient. The enclosed container does not contain any active or sliding seals such as those found in prior art gas spring power supplies or the carbon dioxide compressed gas power supplies discussed earlier. As a result the power supply of the present invention will not leak any of the working gas from inside the enclosed container to outside the enclosed container and will continue to perform without change over an extended period of time. The compressed working gas found in the enclosed container of the present invention can form a stronger and lighter spring than the mechanical springs found in the power supplies of prior art needleless injectors discussed earlier. Since the diaphragm or bellows of the present invention do not have the mass or inertia of the heavier mechanical spring power supplies, the response time for delivery of the stored potential energy of the enclosed container can be quicker. The enclosed container of the present invention does not suffer the physical limitations of mechanical springs related to coil contact or material limitations of mechanical springs related to exceeding the elastic limit of the coil as it approaches full extension or compression. The enclosed volume container of the present invention does not have difficulty in controlling the pressure provided by the working gas which has been a problem for many carbon dioxide compressed gas power supplies. The enclosed container power supply of the present invention can therefore provide accurate dose control for the drug to be delivered.

The power supply of the present invention includes an enclosed container that does not allow leakage of a compressed gas from inside the enclosed container to outside the container. The enclosed container does not have any moving components that move or slide relative to each other and require an active seal to prevent leakage of a compressed gas from leaking to the outside of the enclosed container. Other prior art power supply systems have one or more active seals between a piston and a cylinder that can leak over time due to sudden and rapid movement of the piston relative to the cylinder. The enclosed container of the present invention is capable of changing its volume to a smaller volume as the working gas contained within the enclosed container is compressed to a greater degree of compression placing the enclosed container and the needleless injector is in a loaded state. The enclosed container can change in volume to a larger volume with the working gas in a less compressed state representative of an unloaded state for the enclosed container and the needleless injector.

In one embodiment of the present invention the enclosed container includes a bladder or diaphragm that is formed from a flexible material that is capable of withstanding multiple flexations without forming cracks or weakened areas that could allow leakage of the working gas. The diaphragm is also strong enough to withstand continued exposure to compressed gas that can range in pressure from one to 20 atmospheres. The diaphragm forms at least a part of the surface of the enclosed container that contains a working gas. A portion of the enclosed container can be formed from a rigid material that will not allow leakage of a compressed gas across its surface. A portion of the surface of the enclosed container has a movable surface. This movable surface can be the entire diaphragm, a portion of the diaphragm, or it can be another material that is attached to the diaphragm. The working gas is any gas or combination of gasses that can be compressed to store potential energy and can be expanded to release the stored potential energy. The working gas should not be one that is corrosive or one that is easily leaked through the materials of construction of the enclosed container. Working gasses can include nitrogen, air, carbon dioxide, argon, other gasses, and gas mixtures.

Gasses that can convert to form a liquid when compressed to a pressure representative of the loaded state of the present invention and form a gas in the unloaded state can also be used with the present invention.

The working gas is compressed by interfacing the movable surface of the enclosed container with a reset mechanism. This reset mechanism can be a remote mechanical mechanism as described in one embodiment. The movable surface of the power supply can interface with a hand held mechanical remote reset mechanism and the movable surface moved in a manner to compress the working fluid contained within the enclosed container. This remote mechanical reset mechanism could also be an electromechanical mechanism where the hand operation is replaced by a motor. A hydraulic system or other mechanical system could also provide a remote reset mechanism that could be used to interface with the movable surface of the power supply of the present invention to compress the working fluid. The power supply of the present invention can also interface with a reset mechanism that is a component of the needleless injector of which the power supply is also a component. Such reset mechanisms include screw thread, levers, and other mechanisms as discussed in the prior art section of this disclosure.

As a component of a needleless injector the power supply is held in a compressed or loaded state by interfacing with a mechanical latch, electromechanical latch, or other latch means that is a component of the needleless injector. The latch means interfaces with the movable surface to hold it in a compressed or loaded state. The latch means can be structured such that it is a component of the power supply. With the needleless injector and the power supply in a loaded state, an ampule containing a drug is allowed to interface with the movable surface. In one embodiment of the present invention the movable surface interfaces with the piston of a disposable one-time-use ampule. The disposable drug ampule can include a piston, a cylinder, a sterility seal between the piston and the cylinder, an orifice, and a sterility cover over the orifice. The disposable ampule has a fitting that allows it to be held securely to a mating fitting of the needleless injector such that the piston of the disposable ampule is securely interfacing with the movable surface of the power supply of the needleless injector. The ampule that interfaces with the power supply of the present invention does not have to be a disposable ampule. The ampule can be a reusable ampule that can be removed from the needleless injector, it can be a reusable ampule that is formed as a component of the needleless injector, or it can be another ampule as described earlier in the prior art section.

In one embodiment of the present invention the power supply of the needleless injector is in a loaded state and has an ampule interfacing the movable surface; the needleless injector can be placed onto the cutaneous tissue of the patient. The orifice of the ampule can be placed in direct contact with the skin or a small distance away from the skin as described in the prior art references. A trigger or activation means of the needleless injector is activated resulting in a release of the latch means and allowing the compressed gas contained in the enclosed container to expand to a larger volume. During this expansion the movable surface which interfaces with the drug ampule moves in a direction to force the drug out of the orifice of the drug ampule. The drug flows in a high velocity stream out of the orifice transcutaneously into the underlying tissues of the patient. It is noted that the sterile cover placed over the orifice of the ampule can be removed prior to placing the orifice onto the cutaneous tissue and activating the trigger. The sterile cover can also be formed of a material that can be penetrated by the pressure generated within the ampule following activation of the trigger and the sterile cover can be further removed by the high velocity jet of the drug as it exits the orifice. The material of construction for the sterile cover can be of a biodegradable material. The power supply of the present invention is described as a component of a needleless injector that can be used to deliver a liquid stream of saline. It is understood that the power supply could also be used with a needleless injector that delivers a powered drug, a crystalline drug, a suspension of drug medium, a suspension of microencapsulated drug, or other form of drug that can be delivered by a needleless injector device.

An alternate embodiment for the power supply of the present invention the enclosed container includes a bellows. The bellows can take a generally cylindrical form with the side walls having a corrugated or rippled appearance that can extend or compress in length. An enclosed container that includes a bellows surface of this form can contain a working gas such as those described earlier and undergo a volume change without the presence of an active seal between the inside of the bellows and the outside. The enclosed container of this form can undergo a volume change from a smaller volume as the working gas is in its more compressed state to a larger volume as the gas is allowed to expand to a less compressed state. The bellows can be constructed out of spring metal such as stainless steel, Nitinol, or a metal that has elastic characteristic and can withstand multiple flexations without cracking or fracture. The bellows can also be formed out of a polymeric material, a composite of polymeric material and metal, or another composite material that can withstand multiple flexures and can withstand the pressures of the working gas in its compressed and uncompressed state. The enclosed container can have a portion of its surface that is not expandable and can be constructed of a rigid material. The enclosed container has a moveable surface that can be a portion of the bellows or it can be a surface that is attached to the bellows. The bellows can be formed into a spherical shape or any other shape that will allow an appropriate volume change for the enclosed container.

The power supply of the present invention includes an enclosed container that is capable of changing from a larger to a smaller volume as its contained working gas is compressed from its unloaded state at lower pressure to its loaded state at higher pressure and is capable of changing back to a smaller volume. The movable surface of the enclosed container can move from an unloaded position to a loaded position creating a displacement of the moveable surface from its unloaded position and creating a volume change inside the enclosed container. The pressure applied to a surface area of the movable surface produces a force on the movable surface and is responsible for the storage of potential energy during the compression of the working gas. With the moveable surface in its unloaded position an unloaded force is exerted by the compressed gas onto the moveable surface. This unloaded force can be estimated by knowing the initial or unloaded volume of the enclosed container, the temperature, and applying the ideal gas law, $PV=nRT$, where P is the unloaded pressure or force per unit area exerted on the moveable surface in the unloaded state, V is the unloaded volume of the enclosed container, n is the number of moles contained in the unloaded volume, R is the ideal gas constant of 22.4 liter-atmosphere per mole-degree centigrade, and T is the temperature in degrees Kelvin. The unloaded pressure exerted by the working gas on the movable surface in its unloaded state under a first operating condition of the power supply for the needleless injector will be termed a first unloaded operating pressure.

As the moveable surface undergoes a displacement and a volume change from its unloaded volume, the pressure within the enclosed container increases and the force applied to the moveable surface by the compressed gas also increases resulting in a change in force from its unloaded force. The relationship between the change in force and the percent change in volume is an estimate of a spring constant for the enclosed container such that $\Delta F = K \Delta V/V$, where $\Delta F$ is the change in force from its unloaded force, $\Delta V$ is the change in volume from its unloaded volume, and V is the unloaded volume of the enclosed container, and K is a spring constant for the enclosed container. The relationship between the change in force from its unloaded force and the change in volume from the unloaded volume is an estimate of a spring rate for the enclosed container such that $\Delta F = K' \Delta V$, where $\Delta F$ is the change in force from the unloaded force, $\Delta V$ is the change in volume from the unloaded volume, and K' is the spring rate. It is noted that K and K' also apply to the expansion of the working gas during the activation of the enclosed container needleless injector.

The enclosed container can be filled with additional working gas such that its unloaded operating pressure at the unloaded volume, V, is increased from a first unloaded operating pressure to a higher second operating pressure. Increasing the unloaded operating pressure a small percentage has the effect of increasing the spring constant, K, and increasing the spring rate, K', for the enclosed container approximately a similar percentage. Increasing the area of the moveable surface by a percentage also has the effect of increasing the spring rate, K, and the spring constant, K', for the enclosed container approximately a similar percentage. Increasing the volume of the enclosed container a small percentage without changing the area of the moveable surface will increase the spring rate, K', approximately a similar percentage but will not significantly affect the spring constant, K. Increasing the surface area of the moveable surface by a percentage and increasing the volume of the enclosed container by that percentage squared will increase the spring constant, K, by approximately that percentage but will not significantly affect the spring rate, K'. Making adjustments to the volume of the enclosed container, the area of the moveable surface, and the unloaded operating pressure allows the pressure response of the present power supply to be adjusted to provide the desired loaded and unloaded pressure for a desired displacement of the moveable surface or volume change of the enclosed container. The result is enhanced control in providing a desirable enclosed container pressure versus moveable surface displacement curve for the delivery of drug to the patient. This control will allow the pressure of the drug contained in the ampule to be controlled at a desirable level during drug delivery for with improved effectiveness for the patient treatment.

The enclosed container of the power supply of the present invention can be formed with an additional or adjunct container connected to the enclosed container. This adjunct container can be connected to the enclosed container via a connecting port. The space contained within the adjunct container can flow through the connecting port and into the enclosed container thereby making the space contained within these two containers in fluid communication with each other. The presence of such an adjunct container connected to the enclosed container by a small connecting port can provide the power supply of the present invention with an altered spring constant K and spring rate K' and with an altered time response for the pressure during the activation of the needleless injector. This offers one more variable to adjust the enclosed container pressure versus time curve for drug delivery to the patient.

The enclosed container of the power supply of the present invention can have a fill port present on its surface to provide for adjusting the unloaded operating pressure at its initial or unloaded volume. This fill port has a seal to provide entrance for the working gas but not allow leakage to the outside of the enclosed container. This seal is a static seal, not an active seal between two moving components such as found on the gas springs and carbon dioxide powers supplies of the prior art references.

The enclosed container power supply of the present invention can have more than one-stage of volume and pressure change in going from a loaded volume to an unloaded volume. A two-stage enclosed container power supply of the present invention has a first stage that involves a first volume change from an enclosed container loaded volume to an enclosed container intermediate volume at a higher average pressure. This higher pressure within the enclosed container and within the ampule can provide a larger jet velocity for the drug out of the ampule orifice and enhanced drug penetration through the skin of the patient. The second stage involves a second volume change from the enclosed container intermediate volume to an enclosed container unloaded volume at a lower average pressure. A step change in pressure occurs between the first and second stages. The lower average pressure allows a significant amount of drug to be delivered with a jet of lower velocity and of greater comfort to the patient.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 2A is a partially sectioned view of an enclosed container needleless injector in a loaded state with a diaphragm;

FIG. 2B is a partially sectioned view of an enclosed container needleless injector in a loaded state with a diaphragm and seated with a disposable ampule;

FIG. 4 is a partially sectioned view of an enclosed container needleless injector with an adjunct container;

FIG. 9B is a partially sectioned view of a two-stage enclosed container needleless injector with diaphragm in an intermediate state and seated with a disposable ampule;

DETAILED DESCRIPTION OF THE PREFERRED EMBODIMENTS

Figure 1A:
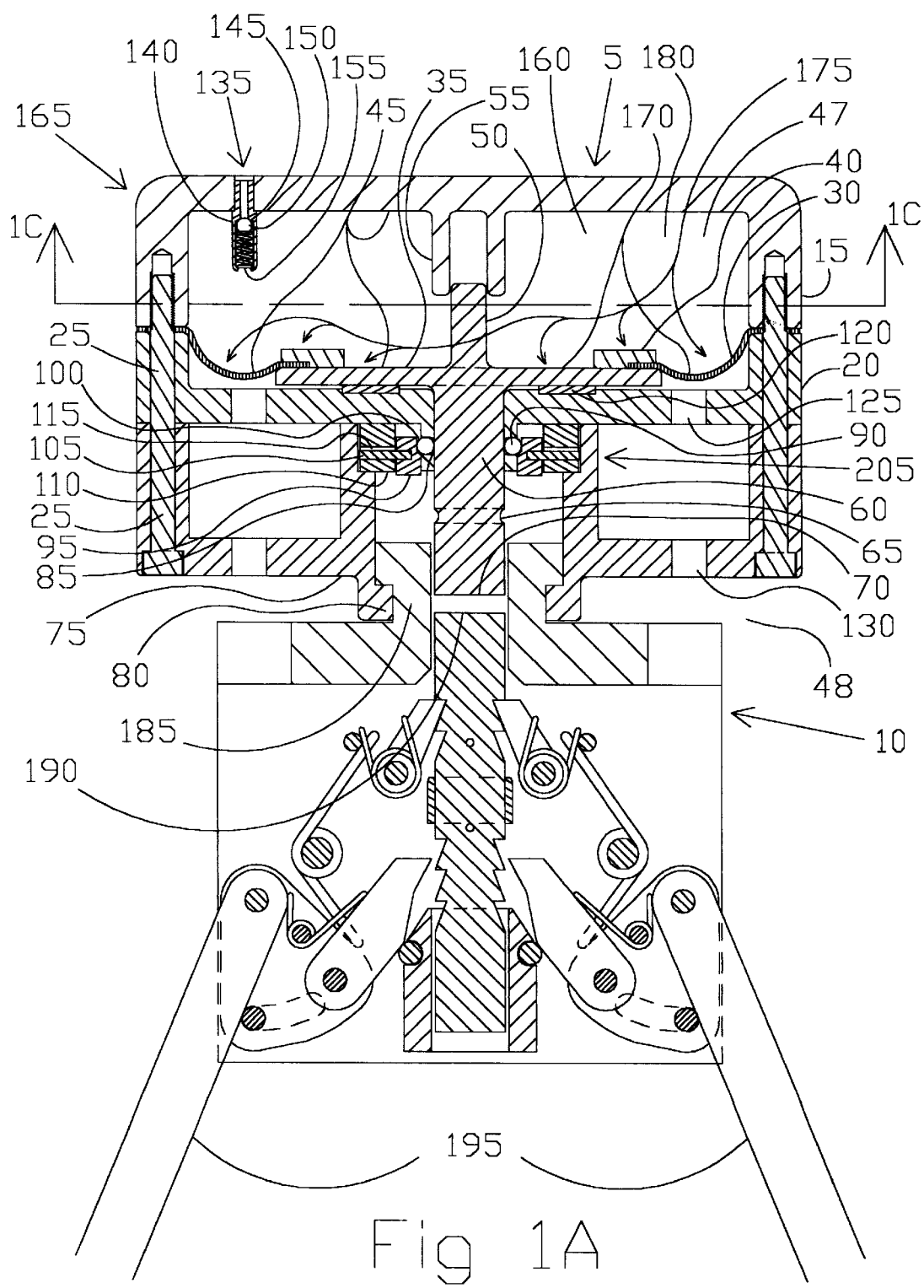
FIG. 1A is a partially sectioned view of an enclosed container needleless injector in an unloaded state with a diaphragm and seated with a remote reset mechanism.
Figure 1B:
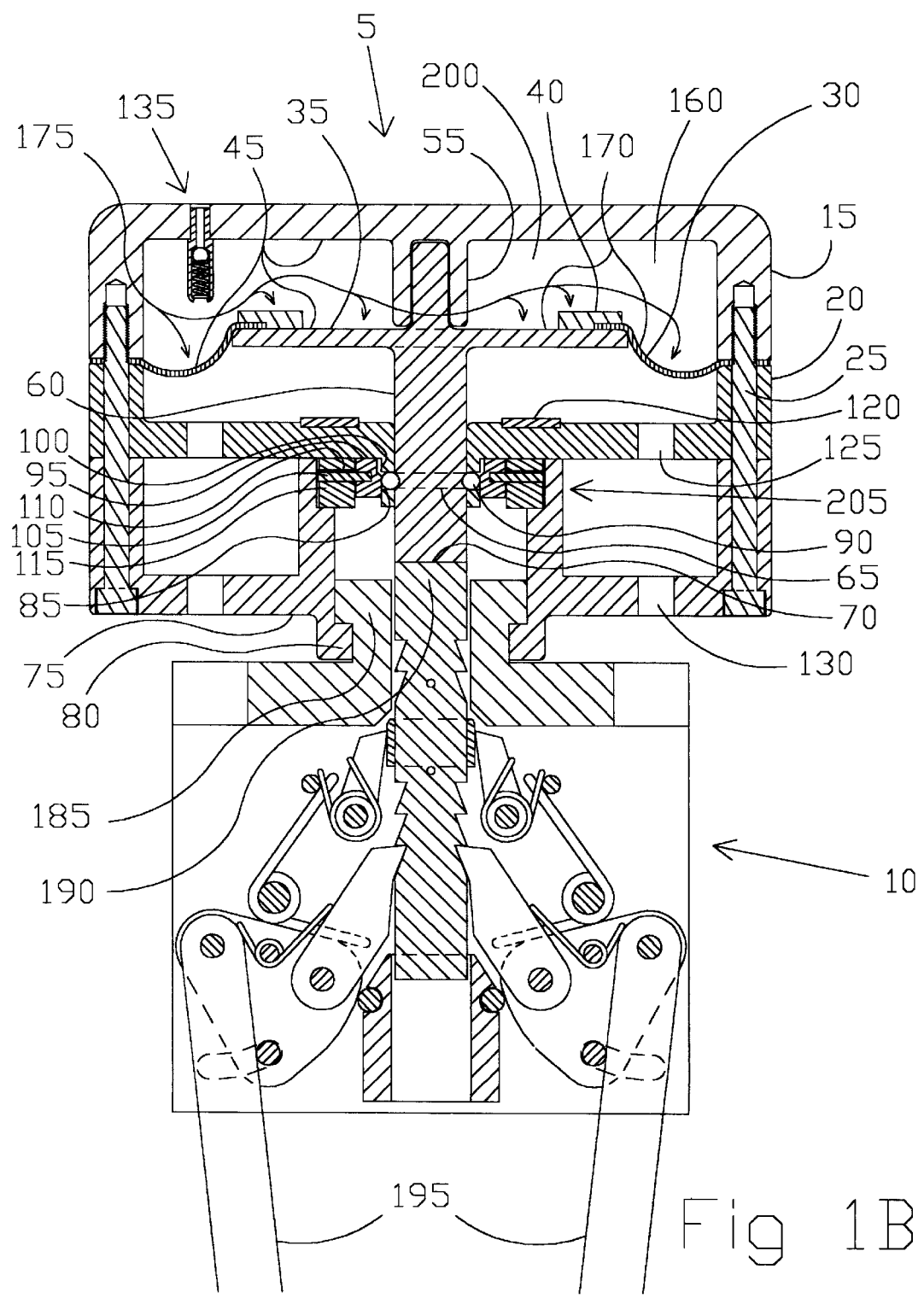
FIG. 1B is a partially sectioned view of an enclosed container needleless injector in a loaded state with a diaphragm and seated with a remote reset mechanism.

FIGS. 1A and 1B show a partially sectioned view of an enclosed container needleless injector 5 interfacing with a remote reset mechanism 10. Reference numerals for all components are found on either FIG. 1A or 1B. An upper diaphragm housing 15 is attached to a lower diaphragm housing 20 with bolts 25 and the upper diaphragm housing 15 and lower 20 diaphragm housings hold a diaphragm 30 in between them without leakage. The diaphragm 30 is held into non-leaking contact with a diaphragm end plate 35 using a clamp ring 40. The diaphragm 30 is a flexible component with enough strength to withstand significant pressure to which it is exposed without significant stretching or rupture. An enclosed container 45 is formed by elements which include the upper diaphragm housing 15, the diaphragm 30 and the diaphragm end plate 35 with an enclosed container inside space 47 and an enclosed container outside space 48. An enclosed container surface is formed by the elements that comprise the enclosed container 45. The enclosed container surface forms an enclosed volume with an inside space 47 without a leakage path from the enclosed container inside space 47 to the enclosed container outside space 48. Attached to one side of the diaphragm end plate 35 is a guide pin 50 that is provided with linear passage within a guide 55 that is attached to the upper diaphragm housing 15. Attached to another side of the diaphragm end plate 35 is a ram 60 with a latch groove 65 and a ram head 70. Attached to the lower diaphragm housing 20 with bolts 25 is a receiver 75 with a receiver head 80. Latching ball holes 85 drilled in the lower diaphragm housing 20 provide passage for latching balls 90. A retainer 95 with a retainer recess 100 and having a trigger pin 105 attached is in contact with the latching balls 90. A trigger 110 has a trigger slot 115 to provide passage for the trigger pin 105. A bumper stop 120 attached to the lower diaphragm housing 20 provides a contact surface with the diaphragm end plate 35 as shown in FIG. 1A. Lower diaphragm housing vents 125 and receiver vents 130 provide venting from the space between the diaphragm end plate 35 and the lower diaphragm housing 20. A fill valve 135 is positioned in the upper diaphragm housing 15. The fill valve 135 includes a valve housing 140 with a valve seat 145, a check ball 150, and a valve spring 155. The fill valve 135 allows a working gas 160 such as nitrogen, air, carbon dioxide, argon, oxygen, or other gasses, gas mixtures, or liquid to gas phase changeable systems to be added to the enclosed container inside space 47 but not allow them to leak out into the enclosed container outside space 48. The fill valve 135 is not an active valve since it does not involve components that are moving during the normal use of the enclosed container needleless injector 5. This is a passive seal that can be capped off if necessary during normal use and it is not required by the present invention. The enclosed container 45 of the present invention has a continuous enclosed container surface since it does not have an active seal from the enclosed container inside space 47 to the enclosed container outside space 48. Other prior art needleless injector devices have one or more active seals that are prone to leakage at the active seal during use. Other prior art gas cylinders used as power supplies for needleless injectors have movement between components during use and therefore have an active seal and therefore do not form a continuous surface. The present enclosed container does not require an active seal between components that are required to move with respect to each other during use and therefore the present enclosed container forms a continuous enclosed container surface. An enclosed container power supply 165 of the enclosed container needleless injector 5 includes the upper diaphragm housing 15, the diaphragm 30, the diaphragm end plate 35, the clamp ring 40, the guide 55, the guide pin 50, and the ram 60 along with the working gas 160 contained within the enclosed container 45. A movable surface 170 for the enclosed container 45 includes the diaphragm end plate 35 and the diaphragm 30. The surface area of the movable surface 170 that is in contact with the working gas 160 is the movable surface area 175. This movable surface 170 is a portion of the enclosed container surface and can move vertically downward or upward along a linear path a shown in FIG. 1A or can move in some other direction so as to provide expansion or compression of the working gas 160 contained in the enclosed container 45. Prior art gas cylinders with active seals are known to form leakage paths for the working gas 160 contained within the cylinder. This leakage is unavoidable due to the high velocity of movement of the piston of such devices with respect to the cylinder with resultant leakage along the active seal during use.

The enclosed container needleless injector 5 has an unloaded state as shown in FIG. 1A and has an enclosed container 45 with an enclosed container unloaded volume 180 and contains the working gas 160 at an unloaded pressure. The unloaded force being exerted by the working gas 160 on the movable surface area is a multiplication product of the unloaded pressure and the movable surface area 175. The receiver head 80 of the needleless injector 5 in an unloaded state can be seated onto a reset head 185 of the remote reset mechanism 10. The ram head 70 of the enclosed container 75 is placed in contact with a reset pusher head 190 of the remote reset mechanism 10. Upon activation of the reset handles 195, the reset pusher head 190 pushes the ram head 70 such that the movable surface 170 moves to compress the working gas 160 within the enclosed container 45. Since activation of the remote reset mechanism 10 results in movement of the movable surface 170, the movable surface 170 can be considered to interface with the remote reset mechanism 10. The needleless injector 5 is put into a loaded state with an enclosed container loaded volume 200 as shown in FIG. 1B. The pressure in the enclosed container 45 will increase to a loaded pressure that can be estimated by using the ideal gas law stated earlier in the summary section of this disclosure. The loaded force being exerted upon the movable surface 170 by the working gas 160 is the multiplication product of the loaded pressure and the movable surface area 175. The enclosed container needleless injector 5 of the present invention is generally intended to be a reusable device, however the simplicity of the design of the enclosed container power supply 165 of the present invention offers the opportunity for this enclosed container needleless injector 5 or this enclosed container power supply 165 to be a disposable, one time use device. As a disposable device, the enclosed container needleless injector 5 could be provided in a loaded state without the need for resetting the enclosed container power supply 165. The working gas 160 contained in the enclosed container 45 would be required to undergo an expansion to provide the force necessary to deliver a drug transcutaneously to the patient.

This process of resetting the needleless injector 5 to a loaded state can be accomplished using a remote reset mechanism 10 of a mechanical, electromechanical, hydraulic, or other reset means. This resetting process can also be accomplished with a built-in reset mechanism included as a component of the needleless injector 5 such as a the screw thread, lever, hydraulic, or other reset means including those found in the prior art patent references and discussed earlier. As shown in FIGS. 1A and 1B the ram 60 provides contact with the remote reset mechanism 10, however it is understood that the reset pusher head 190 could be configured to contact directly with the movable surface 170. Further, the ram 60 can be considered as a component of the movable surface 170. It is therefore understood that the movable surface 170 interfaces with the remote reset mechanism 10 or with a reset means. Once the needleless injector 5 is in the loaded state, the remote reset mechanism 10 can be removed by unseating the receiver head 80 from the reset head 185.

As the enclosed container needleless injector 5 moves from its unloaded state to its loaded state, the ram 60 moves with respect to the latching balls 90 until the latch groove 65 is aligned with the latching balls 90 as shown in FIG. 1B. The latching balls 90 travel through the latching ball holes 85 and are held in place by the retainer 95 to hold the ram 60 in this loaded position with the movable surface 170 being held from further movement and the enclosed container 45 having an enclosed container loaded volume 200. A latch mechanism 205 used to hold the ram 60 in this loaded position includes the latching balls 90, the latching ball holes 85, and the retainer 95. Other forms of mechanical or non-mechanical latches could as easily have been used to form a latch means that holds the movable surface 170 such that the enclosed container 45 contains the working gas 160 at a loaded pressure and at an enclosed container loaded volume 200. Since the latch mechanism 205 or latch means prevents the movable surface from undergoing any movement when it is latched, the latch mechanism 205 car be considered to interface with the movable surface 170. The latch mechanism 205 is shown in FIG. 1B to directly contact the ram which in turn is attached to the diaphragm end plate 35. It is understood that the latch mechanism 205 or a latch means can be configured to directly contacted the diaphragm end plate 35; it is further understood that the ram 60 can be considered as a component of the movable surface 170; therefore the moveable surface 170 is understood to interface with the latch mechanism 205 or latch means.

Figure 1C:
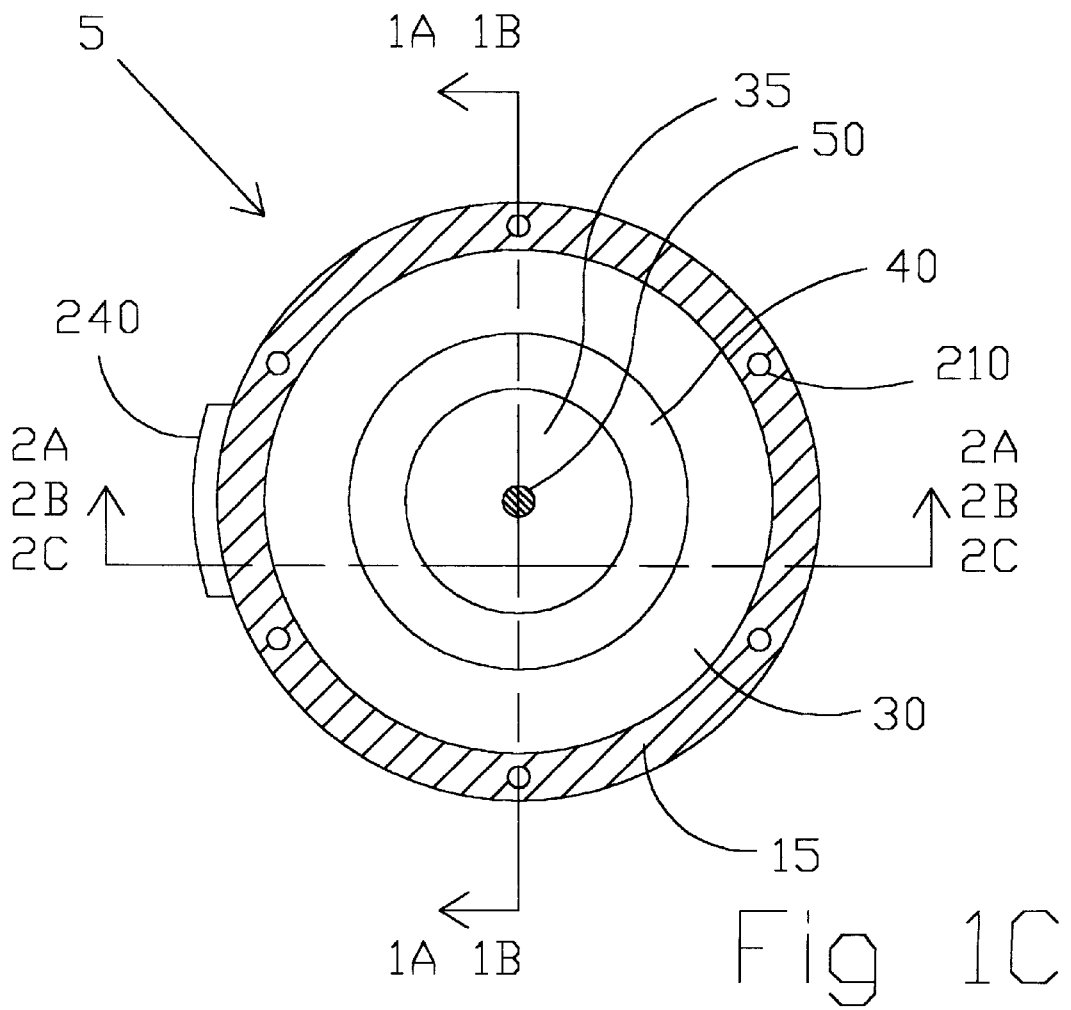
FIG. 1C is a sectional view of an enclosed container needleless injector with a diaphragm.

FIG. 1C is a sectional view of the enclosed container needleless injector 5 shown in FIGS. 1A and 1B. Bolt holes 210 in the diaphragm 30 accommodate the bolts 25 shown in FIGS. 1A and 1B. Also shown is the guide pin 50, the diaphragm end plate 35, and the clamp ring 40. Other reference numerals are as shown in FIGS. 1A and 1B. A sectional view 90 degrees out of phase with FIGS. 1A and 1B show the trigger 110 and trigger slot 115 more clearly (see FIGS. 2A–2C).

Figure 2C:
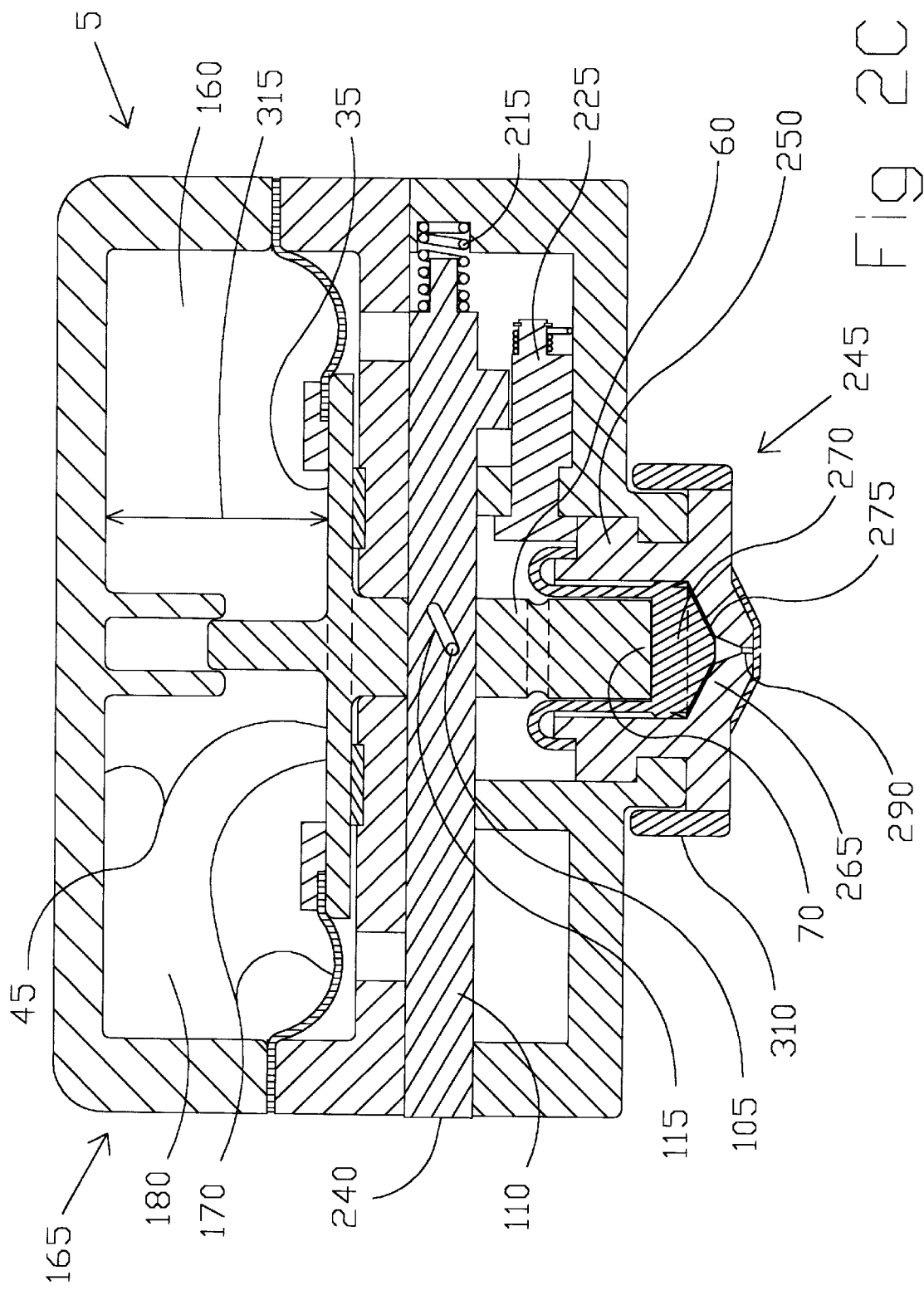
FIG. 2C is a partially sectioned view of an enclosed container needleless injector in an unloaded state with a diaphragm and seated with a disposable ampule.

FIGS. 2A–2C show sectional views of the enclosed container needleless injector 5 rotated 90 degrees from the views shown in FIGS. 1A and 1B. FIG. 2A shows the enclosed container needleless injector 5 in a loaded state without any thing seated in its receiver head 80. A trigger 110 with a trigger slot 115 is positioned adjacent and below the upper diaphragm housing 15. Contained within the trigger slot 115 is the trigger pin 105 which is attached to the retainer 95 (see FIGS. 1A and 1B). The trigger 110 is seated with a trigger spring 215 which is compressed and being held by a receiver recess 220. A safety link 225 is included in the enclosed container needleless injector 5 to ensure that the trigger 110 cannot be activated without any thing in its receiver head 80. The safety link 225 has a safety link lock 230 that prevents a trigger key 235 from moving to the right as a trigger button 240 is pushed. A safety link tab 241 is used to facilitate rotational movement of the safety link 225. A snap ring 242 serves to hold safety link spring 243 onto safety link 225. Safety link spring 243 is seated in a safety link seat 244 to ensure that safety link 225 prevents trigger key 235 from moving when receiver head 80 is empty. Other reference numerals found in FIG. 2A correspond to the elements previously or otherwise described in FIGS. 1A and 1B.

FIGS. 2B and 2C show the enclosed container needleless injector 5 with a disposable ampule 245 seated with it. As shown in FIG. 2B the disposable ampule 245 has an ampule head 250 that is seated with the receiver head 80 of the enclosed container needleless injector 5 in a loaded state. The safety link 225 has rotated from its position in FIG. 1A to allow trigger 110 to move to the right if trigger button 240 is pushed. Rotation of the safety link 225 due to seating of disposable ampule 245 occurs by contact of the ampule head 250 with the safety link tab 241 (shown in FIG. 2A). The ampule housing 255 could be made out of a polymer such as polycarbonate, acrylic, polyurethane, other polymers, block copolymers, reinforced polymers, a composite of more than one polymer, or a composite of a polymer and one or more other materials. Additionally the disposable ampule 245 could be formed in part out of glass, ceramic, saphire, other precious jewels, carbon, or other non-polymeric materials either by themselves, combining two or more of these non-polymeric materials, or combining one or more of these non-polymeric materials with one or more polymeric materials.

The ampule housing 255 has an ampule cylinder 260 with a biocompatible surface to contact with the drug in order to prevent loss of drug activity, to prevent drug denaturation, and to prevent drug contamination. The ampule cylinder 260 which has a conically shaped ampule cylinder head 265 can include a thin coating of a material compatible to the drug to ensure long term drug viability. An ampule piston 270 which has an ampule piston head 275 can be formed of a softer polymeric or non-polymeric material than the ampule housing 255. The ampule piston 270 can also include a thin coating of a material that is compatible to the drug to ensure long term drug viability. An ampule volume 280 contained between the ampule piston 270 and the ampule cylinder 260 provides a reservoir space for containment of the drug that is to be delivered to the patient. The same group of materials applies to the structure of the ampule piston 270 as applies to the ampule housing 255. The ampule piston 270 can have a piston active seal 285 found on the ampule piston 270 to help form a seal and prevent leakage from between the ampule piston 270 and the ampule cylinder 260 during the delivery of the drug. As the ampule piston 270 moves to expel the drug contained within the ampule volume 280, the piston active seal 285 is forced out against the ampule cylinder 260 to create an enhanced seal due to the outward movement of the piston active seal 285.

An orifice 290 is formed, located, or positioned in the ampule housing 255. This orifice 290 can range in diameter from approximately 0.001 inches to 0.014 inches and preferably the diameter ranges from 0.003 to 0.009 inches. Saphire orifice or orifice 290 made from metal could be insert molded into a polymeric ampule housing 255 to form a suitable disposable ampule 245. A conical orifice entrance 295 allows a flow of drug into the orifice 290 from the ampule volume 280 to be more efficient from many standpoints. The pressure drop from the ampule volume 280 to downstream of the orifice for a specific flow rate will be less thereby requiring less energy from the needleless injector 5 and allowing the needleless injector 5 to therefore be smaller or lighter for the same drug delivery rate and volume. Shear induced trauma or damage to the drug will be less thereby providing the drug with a greater activity and requiring less drug to accomplish the same result in the patient. The resultant high velocity stream exiting the orifice 290 will be more columnated as it exits the orifice 290. This can provide a better penetration of the drug stream through the cutaneous tissue with less pain and trauma to the patient.

The ampule has a security seal 300 that connects the ampule piston 270 with the ampule housing 255 and ensures that sterility is maintained within the drug contained within the disposable ampule 245. The ampule has a sterility cover 305 that covers the orifice 290 to provide sterility protection and prevent drug evaporation, denaturation, or contamination. The sterility cover 305 can be reversibly adhered to the ampule housing 255 and removed prior to seating the ampule head 250 in the enclosed container needleless injector 5 receiver head 80. Alternately, the sterility cover 305 can be formed out of a polymeric material that provides a sterile barrier and can be ruptured upon exposure to high pressure as found in the ampule volume 280 after activation of the needleless injector 5. A polymeric sterility cover 305 can be applied to the ampule housing 255 by dip coating or applying a liquid polymer onto a portion of the ampule housing 255 containing the orifice 290. The liquid polymer will cover the orifice 290 and cure to form a sterility cover 305. The polymeric material of the sterility cover 305 would have to be approved for medical implant and may be biodegradable such that any particulate that may be generated by and entrained in the high velocity drug stream may be carried along with the drug stream into the patient. An ampule outer body 310 allows the ampule head 250 to be properly seated with the receiver head 80 using digital manipulation.

A reusable ampule (not shown) could be configured similarly to the disposable ampule 245 for use in the needleless injector 5 of the present invention. Alternately, an ampule (not shown) with similar structure to the disposable ampule 245 can be built in as a component of the enclosed container needleless injector 5 in a manner similar to the assembly shown in FIG. 2B or similar to those injectors described in the prior art discussed earlier. The disposable ampule 245 or a reusable ampule can be considered a reservoir means that interfaces with the enclosed container needleless injector 5.

As the ampule head 250 of the disposable ampule 245 is seated with the receiver head 80 as shown in FIG. 2B, the ampule head 250 is placed into contact with the safety link 225 causing it to rotate. Rotation of the safety link 225 causes the safety link lock 230 to move out of contact with the trigger key 235. This feature ensures that the trigger 110 cannot be activated unless a disposable ampule 245 or other ampule is seated in the needleless injector 5. The ram head 70 is shown in direct contact with or adjacent to the ampule piston 270. A gap or spacing can be configured between the ram head 70 and the ampule piston head 275 to provide the ram 60 with an opportunity to accelerate before contacting with the ampule piston 270. Such acceleration can offer a pressure impulse or a pressure spike at the initiation of drug delivery and can enhance penetration of the stream of drug into the patient.

The enclosed container needleless injector 5 can be placed adjacent to the cutaneous tissue of the patient with the orifice 290 either in contact with the skin or spaced a small distance away. A small spacer (not shown) attached to the receiver 75 of the enclosed container needleless injector 5 could provide a spacing that could range from 0.1 to 4.0 millimeters in length. Activation of the enclosed container needleless injector 5 occurs by pushing the trigger button 240 causing the trigger 110 or other activation means to move to the right as shown in FIG. 2C forcing the trigger pin 105 downward and unlatching the latch mechanism 205. The movable surface 170 moves downward due to the loaded pressure found in the enclosed container loaded volume 200. The working gas 160 undergoes an expansion as the enclosed container expands from a smaller enclosed container loaded volume 200 to a larger enclosed container unloaded volume 180. Movement of the movable surface 170 causes the ram head 70 to push against the ampule piston 270 and forces the drug out of the orifice 290 at a high velocity that penetrates the cutaneous tissue of the patient and delivers the drug to the underlying tissues of the patient. Mechanical activation means other than the trigger 110 described in this disclosure can be activated to allow movement of the movable surface 170 and allow the working gas 160 to expand to a larger volume.

Since movement of the movable surface 170 results in a movement of the ampule piston 270 of the disposable ampule 245 or reservoir means, the movable surface 170 is understood to interface with the disposable ampule 245 or reservoir means. Movement of the diaphragm end plate 35 causes the ram 60 to move and directly contact the ampule piston 270 in a manner so as to push the drug out of the orifice 290. It is understood that the diaphragm end plate 35 can be configured to have direct contact with the disposable ampule 245 to apply a loaded force onto the disposable ampule 245 or drug reservoir to cause the drug to be expelled from the disposable ampule 245 or drug reservoir. Further, it is understood that the ram 60 can be considered as a component of the movable surface 170. Therefore it is understood that the disposable ampule 245 or reservoir means interfaces with the movable surface 170. The latch mechanism 205 as shown in FIG. 1B or other latch means which can be a component of the enclosed container needleless injector 5 can interface with the ampule piston 270 or other component of the disposable ampule 245 to hold the enclosed container needleless injector 5 and the enclosed container power supply 165 in a loaded state. Release of the latch means allows the ampule piston 270 or other component of the disposable ampule 245 to be released and allow delivery of the drug contained within the ampule.

FIG. 2C shows the enclosed container needleless injector 5 in an unloaded state with an enclosed container unloaded volume 180 and an enclosed container length 315. The trigger spring 215 has been further compressed and the safety link 225 has been rotated due to the movement of the trigger 110 to the right from its position in FIG. 2B. The ampule volume 280 has been reduced to approximately zero as the ampule piston head 275 is in contact with the ampule cylinder head 265. Following activation of the enclosed container needleless injector 5 and return of the enclosed container 45 to an enclosed container unloaded volume 180, the disposable ampule 245 can be removed as shown in FIG. 2A. During resetting the trigger 110 returns to an inactivated position and the safety link 225 is rotated to a position as shown in FIG. 2A. The enclosed container needleless injector 5 is ready for resetting.

Figure 3:
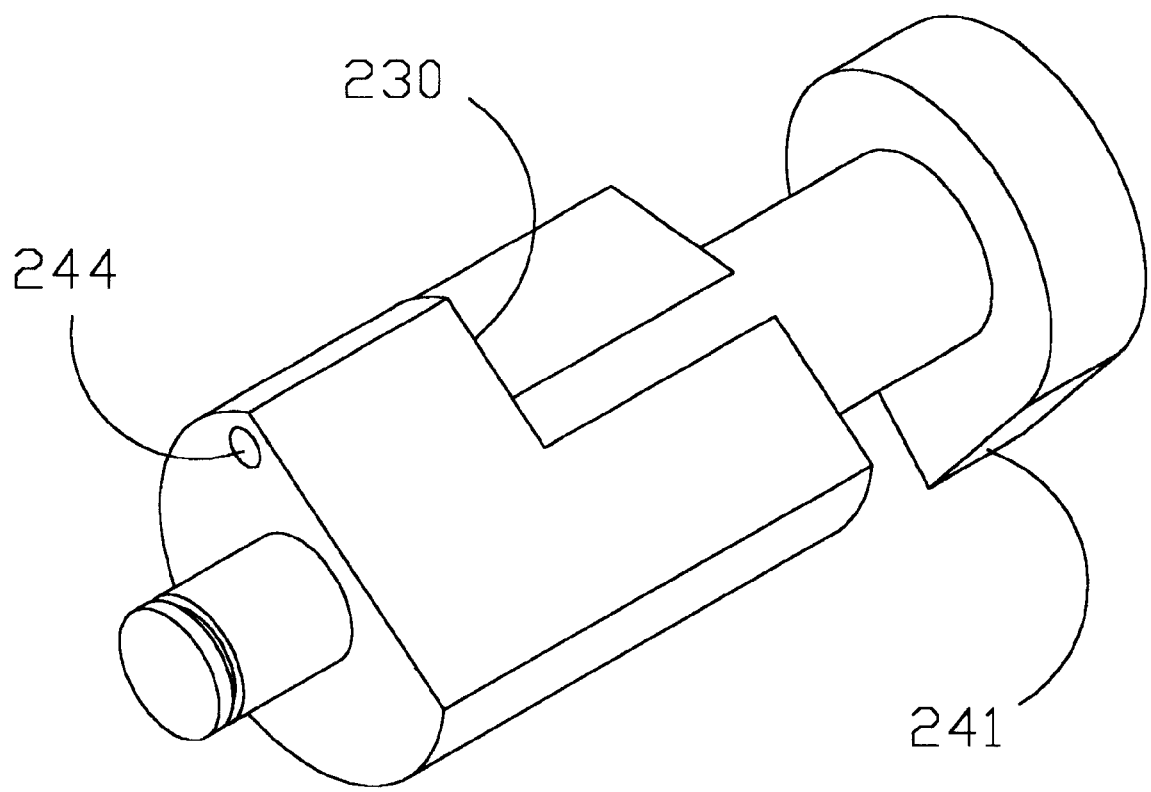
FIG. 3 is an isometric view of a safety link for an enclosed container needleless injector with a diaphragm.

An isometric view of the safety link 225 with the safety link lock 230 is shown in FIG. 3. The safety link lock 230, safety link tab 241, and safety link seat 244 are shown.

FIG. 4 is a partially sectioned view of an enclosed container needleless injector 5 with an adjunct container 320. The adjunct container 320 can be a fixed volume container that is attached to the enclosed container needleless injector 5 or it can utilize any unused closed container volume. A stroke length 325 for the diaphragm end plate 35 represents the approximate displacement for the movable surface 170. The adjunct container 320 is connected to the enclosed container 45 by a connecting port 330. Working gas 160 contained in the enclosed container 45 can flow into the adjunct container 320 and the working gas 160 can flow back from the adjunct container 320 to the enclosed container 45. Lower diaphragm housing side vents 327 provide venting from the space between the diaphragm end plate 35 and the lower diaphragm housing 20. The connecting port 330 can be a large or small diameter opening with a length to provide a pathway for gas or fluid flow. It is understood that the adjunct container 320 is in fluid communication with the enclosed container 45 since the connecting port 330 connects the adjunct 330 and enclosed 45 containers in a fluid tight manner. More than one adjunct containers (not shown) can be connected to the enclosed container 45 with more than one connecting ports (not shown) and still fit under the teachings of this device disclosure. The enclosed container power supply 335 for the enclosed container needleless injector 5 of FIG. 4 includes the adjunct container 320 in addition to the other components included in the enclosed container power supply 165 as discussed in FIGS. 1A and 1B. The presence of an adjunct container 320 can provide the enclosed container needleless injector 5 with a smaller profile or smaller shape by using space or volume that was available for this use and provide an altered spring rate.

The size and shape of the enclosed container needleless injector 5 shown in FIGS. 1A–1C is similar to a flattened cylinder or a hockey puck. This conformation provides a needleless injector 5 device that is easily carried by the patient such that drug delivery can be performed by the patient throughout the day outside the home. The movable surface area 175 can be a large percentage of the total surface area in contact with the working gas 160 in the enclosed container 45. In transforming from an enclosed container unloaded volume 180 to an enclosed container loaded volume 200 the enclosed container 45 undergoes a volume change. The pressure within the enclosed container 45 is transformed from an unloaded pressure to a loaded pressure. This change in pressure multiplied by the movable surface area 175 gives the change in force exerted on the movable surface 170 in going from an enclosed container unloaded volume 180 to an enclosed container loaded volume 200.

As an example of how the spring rate K' and spring constant K for one embodiment of the enclosed container 45 can vary with changes in the pressure of the working gas 160, movable surface area 175, or enclosed container unloaded volume 180, the following example is discussed. This analysis is only an estimate and applies to small changes in volume in comparison to the enclosed container unloaded volume 180. A spring rate, K', for the enclosed container 45 describes the ratio of the change in force exerted on the movable surface 170 by the working gas 160 with respect to the change in volume of the enclosed container 45 in going from an enclosed container unloaded volume 180 to an enclosed container loaded volume 200. The spring constant, K, for the enclosed container 45 describes the ratio of the change in force exerted on the movable surface 170 with respect to the percentage change in volume of the enclosed container 45. For a small change in volume with respect to the volume of the enclosed container 45, changes to K' and K can be estimated. An increase in the unloaded pressure within the enclosed container 45 by a percentage, or an increase in the movable surface area 175 by that percentage can increase the spring rate and spring constant by approximately a similar percentage. An increase in the enclosed container unloaded volume 180 by a percentage while maintaining the movable surface area 175 at a constant value can reduce the spring rate by approximately a similar percentage and maintain the spring constant at approximately a constant value. An increase in the enclosed container movable surface area 175 from a smaller to a larger area with a specific ratio of smaller to larger enclosed container movable surface area 175, and at the same time providing an increase in the enclosed container unloaded volume to form a similar specific ratio will increase the spring constant by approximately a similar specific ratio and maintain the spring rate at approximately a constant value. From this analysis it is seen that changing the conformation of the enclosed container needleless injector 5 through a change in movable surface area 175, a change in the enclosed container unloaded volume 180, or a change in the unloaded pressure can affect the force that is delivered by the movable surface 170 onto the disposable ampule 245 and can affect the change in force imposed on the movable surface 170 by the working gas per change in enclosed container volume during the delivery of the drug from the ampule. For the previously discussed enclosed container power supply 165 of the present invention with a diaphragm 30 a change in volume for a cylindrically shaped volume can be equal to the movable surface area 175 multiplied by a change in axial displacement or stroke length 325 as the movable surface 170 moves throughout its stroke length 325. A similar analysis to this can be applied equally well to other embodiments of the present invention including those shown in FIGS. 5A and 5B.

In this disclosure interface of the movable surface 170 with the disposable ampule 245 or reservoir means is understood to mean that either there is direct contact or there is contact through one or more intermediate components between the movable surface 170 and the disposable ampule 245 such that movement of the movable surface during expansion of the compressed working gas 160 from a smaller enclosed container loaded volume 200 to a larger enclosed container unloaded volume 180 causes a direct or similar movement within the disposable ampule 245 to cause the drug contained with the disposable ampule 245 to be expelled. Interface between the movable surface 170 and a reset means is understood to mean that the movable surface 170 is in direct contact or there is contact through one or more intermediate components with the reset pusher head 190 or a reset pusher means such that movement of the reset pusher head 190 or reset pusher means results directly in movement of the movable surface 170. Interface of the movable surface 170 with the latch mechanism 205 or a latch means is understood to mean that the latch mechanism 205 or a latch means is in direct contact with the movable surface 170 or there is one or more direct intermediate components between the latch mechanism 205 or a latch means and the movable surface 170 such that activation of the latch mechanism 205 or latch means directly results in lack of movement of the movable surface 170. It is also understood that although the latch mechanism 205 or a latch means is included in the needleless injector and interfaces with the movable surface 170 of the enclosed container power supply 165, the latch mechanism 205 or a latch means can be included with the enclosed container power supply 165 and require the latch mechanism 205 to interface with a component of the enclosed container needleless injector 5.

Figure 5A:
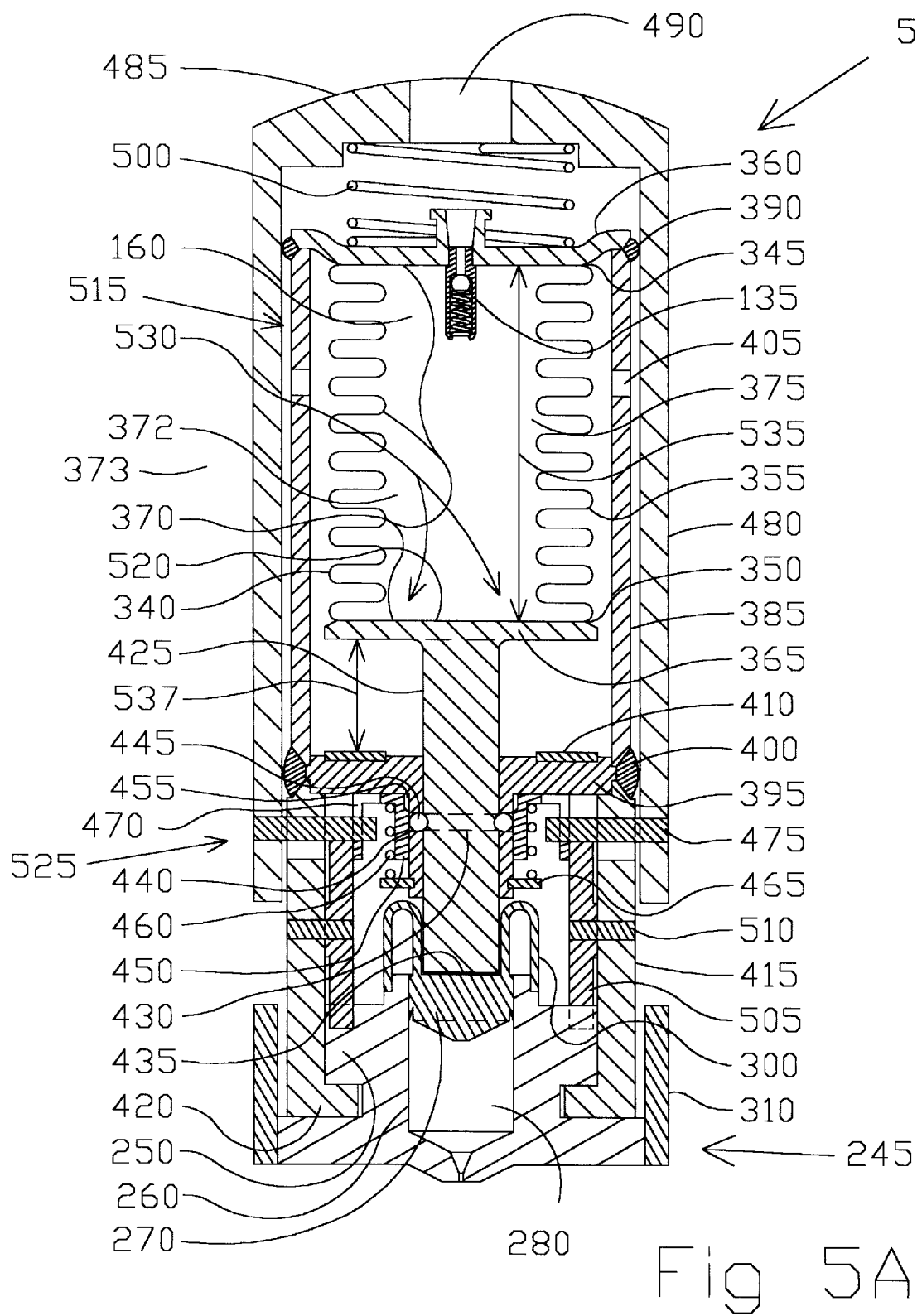
FIG. 5A is a partially sectioned view of an enclosed container needleless injector in a loaded state with a bellows and seated with a disposable ampule.
Figure 5B:
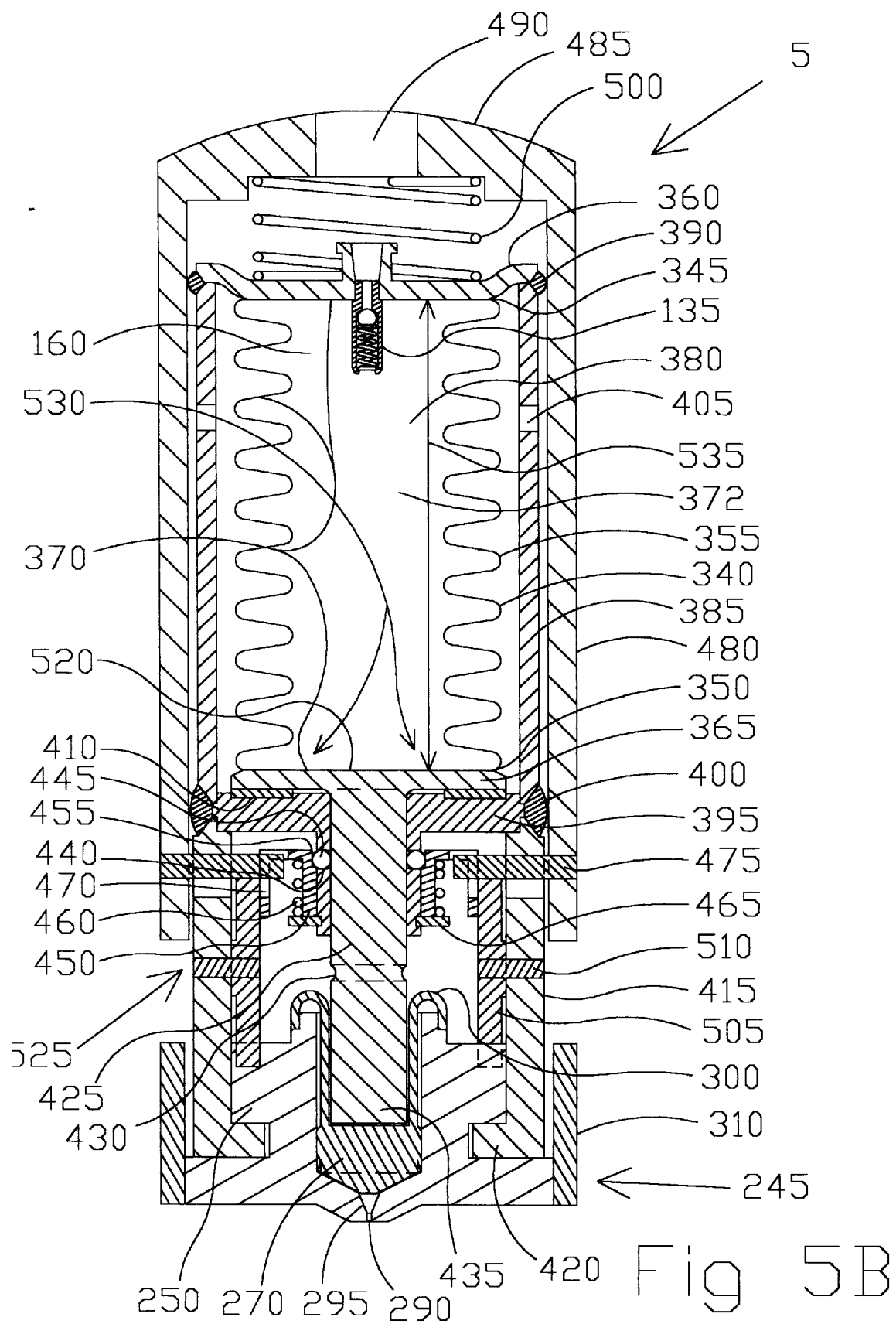
FIG. 5B is a partially sectioned view of an enclosed container needleless injector in an unloaded state with a bellows and seated with a disposable ampule.
Figure 5C:
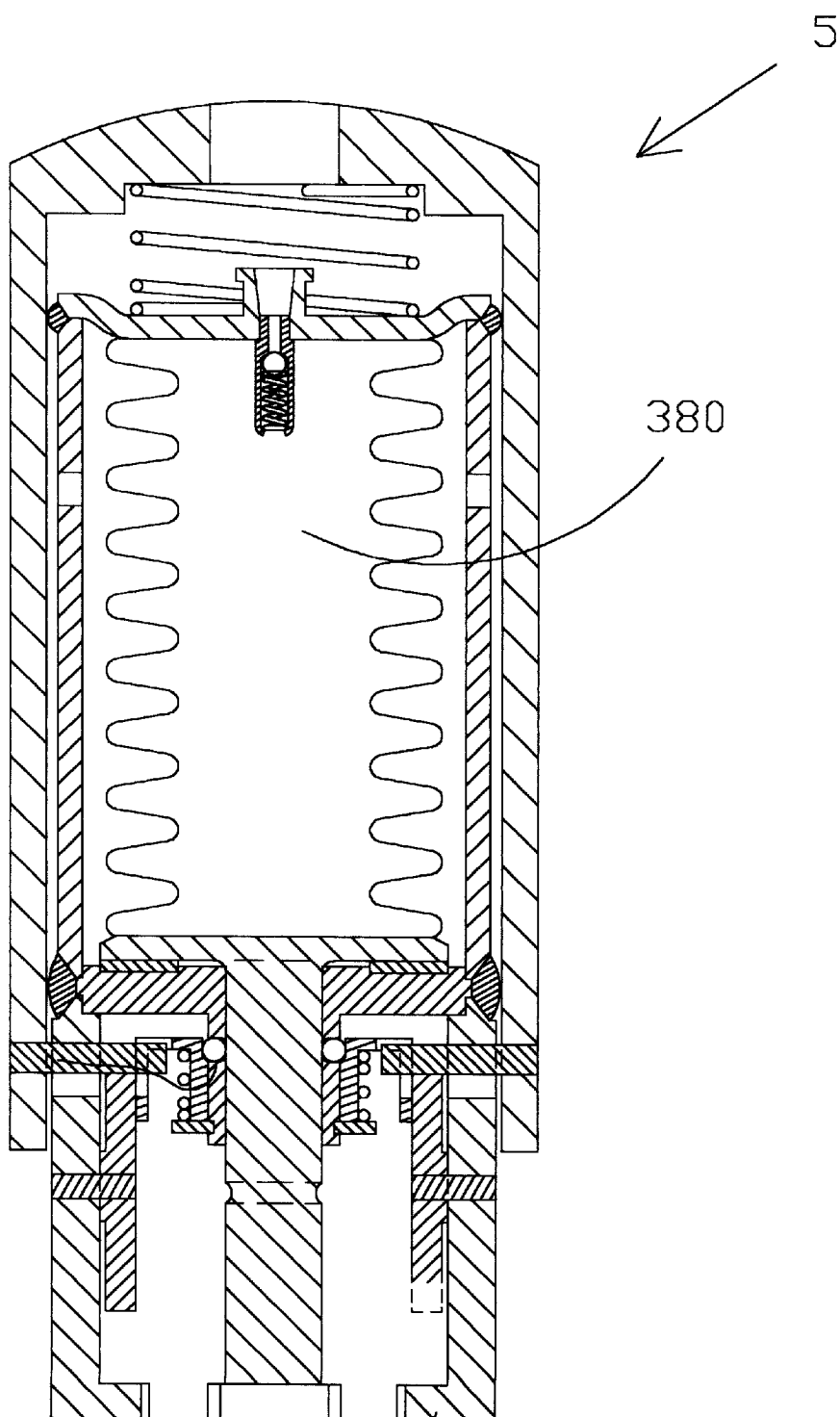
FIG. 5C is a partially sectioned view of an enclosed container needleless injector in an unloaded state with a bellows.

A preferred embodiment for the enclosed container needleless injector 5 seated with a disposable ampule 245 is shown in FIGS. 5A and 5B and without the disposable ampule 245 in FIG. 5C. Many components for the enclosed container needleless injector 5 bear the same name and the same function to the components described in FIGS. 1A, 1B, 2A, 2B, and 2C, however their appearance may be different and are therefore assigned different reference numerals. The operation of the embodiment shown in FIGS. 5A and 5B has a similar operation as described earlier for the embodiment shown in FIGS. 1A, 1B, and 2A–C.

A bellows 340 with an upper bellows end 345, a lower bellows end 350, and a corrugated side wall 355 is attached at the upper bellows end 345 to an upper bellows housing end plate 360 and at the lower bellows end 350 to a ram plate 365. The bellows 340 can be constructed from a spring metal with good flexure properties that will not lead to cracking or rupture. The bellows 340 can be constructed out of stainless steel, Nitinol, or other metal. The bellows 340 could also be constructed out of a polymeric material that has been reinforced with another polymeric or with a non-polymeric material to provide strength. A fiber reinforced polymeric or a metal reinforced polymeric material could be used to form the bellows 340.

The upper bellows end plate 360, the ram plate 365, and the corrugated side wall 355 form an enclosed container 370 defining an enclosed container inside space 372 and an enclosed container outside space 373 and containing an enclosed container loaded volume 375 (see FIG. 5A) or an enclosed container unloaded volume 380 (see FIG. 5B) inside the enclosed container 370. The enclosed container 370 has an enclosed container surface that is formed by the elements of the enclosed container 370. The enclosed container surface completely encompasses the enclosed container inside space 372 and forms a continuous surface without an active seal. The enclosed container 370 is capable of changing in volume and does not have any active seal extending from the enclosed container inside space 372 to the enclosed container outside space 373. The enclosed container surface is a continuous surface which can include a passive seal between two components that are not required to move with respect to each other during normal use, but the enclosed container surface is continuous since it does not include any active seals requiring movement between components during use. The bellows 340 is housed within a bellows housing 385 that is attached to the upper bellows housing end plate 360 with a weld 390 or other suitable attachment means and to a lower bellows housing end plate 395 with a weld 400 or other suitable attachment. It is understood that a bellows means can be identified to include the bellows and other components sealingly attached to it such as the ram plate 365. A bellows means thus provides a movable surface such as the ram plate 365 with an ability to move linearly or otherwise due to movement of the bellows 340 during volume expansion or compression of the working gas 160. A bellows housing vent 405 provides access for the space contained between the bellows 340 and the bellows housing 385 to atmospheric pressure. The lower bellows housing end plate 395 has a bumper stop 410 attached to provide for a cushioned contact with the ram plate 365. A receiver 415 with a receiver head 420 is attached to the lower bellows housing end plate 395. The ram plate 365 is attached to a ram 425 having a latch groove 430 and a ram head 435. Latching ball holes 440 drilled into the lower bellows housing end plate 395 provide passage for latching balls 445. As shown in FIGS. 5A and 5B a retainer 450 with a retainer recess 455 provides contact with the latching balls 445. A latch spring 460 is held under compression by the retainer 450 and a snap ring 465. A retainer slot 470 provides passage for a trigger pin 475 that is attached to a trigger 480 with a trigger cap 485 and an access hole 490 in the trigger cap 485. A fill valve 135 located on the upper bellows housing end plate 360 has the same structure and function as the fill valve 135 shown in FIGS. 1A and 1B and bears the same reference numeral. A trigger spring 500 extends between the trigger cap 485 and the upper bellow housing end plate 360. A safety link 505 is pivotally connected about a safety link pivot 510 to the receiver 415.

The enclosed container power supply 515 for the embodiment shown in FIGS. 5A and 5B includes the bellows 340, the upper 360 and lower 395 bellows housing end plates, the ram plate 365, and the ram 425 along with the working gas 160 contained in the bellows 340. The movable surface 520 for the enclosed container 370 is a portion of the enclosed container surface and includes the ram plate 365. The movable surface could have been designed such that it did not include the ram plate 365. The movable surface 520 can move in a vertical direction with a linear path as shown in FIG. 5A or the movement can be in another direction or in more that one direction. The movable surface 520 can also include the ram 425. A disposable ampule 245 with an ampule head 250 is shown seated with the receiver head 420 of the enclosed container needleless injector 5 (see FIG. 5A). Reference numerals for the disposable ampule 245 are the same as those used in FIGS. 2A–2C.

In FIG. 5A the enclosed container needleless injector 5 is in a loaded state with the enclosed container 370 having the enclosed container loaded volume 375. Prior to achieving the loaded state it is understood that the receiver head 420 of the enclosed container needleless injector 5 was seated with the reset head 185 of the remote reset mechanism 10 in a manner similar to that shown in FIGS. 1A and 1B. Also, as shown in FIGS. 1A and 1B, the reset pusher head 190 pushed the ram head 435 and the ram plate 365 upward until the latching balls 445 engaged the latching groove 430 as shown in FIG. 5A. The remote reset mechanism 10 or other remote reset means can be used to reset the enclosed container needleless injector 5. Alternately, a reset means can be included as a component of the needleless injector 5 and used to reset the needleless injector 5 to a loaded state. The remote reset mechanism 10 or other reset means is understood to interface with the movable surface resulting in its movement to a loaded position. With the needleless injector in the loaded state, the retainer 450 moves upward into contact with the lower bellows housing end plate 395 and holds the latching balls 445 securely in the latching groove 430 such that the ram 425 holds the ram plate 365 in position as shown in FIG. 5A. The movable surface 520 is held in a loaded position due to a latch mechanism 525 that includes the latching balls 445, the retainer 450, and the latch spring 460. The latch mechanism 525 could be any mechanical or other latch means that serves to hold the movable surface 520 in place. The latch mechanism 525 or latch means can interface with the movable surface 520 to hold it in the loaded state. The latch mechanism 525 or other latch means of the enclosed container needleless injector 5 can interface with the ampule piston 270 or other component of the disposable ampule 245 to hold the enclosed container needleless injector 5 or the enclosed container power supply 335 in a loaded state and can be released to allow activation of the enclosed container needleless injector 5 and delivery of drug from the disposable ampule 245.

The enclosed container loaded volume 375 contains the working gas 160 at a loaded pressure. The enclosed container 370 with working gas 160 at a loaded pressure exerts a loaded force on the movable surface 520. The ampule head 250 of the disposable ampule 245 can be seated onto the receiver head 420 of the enclosed container needleless injector 5 in a manner shown in FIG. 5A. The ampule piston 270 is brought into contact with the ram head 435. A space or gap (not shown) can be maintained between the ampule piston 270 and the ram head 435 prior to activation of the needleless injector 5 to provide an altered pressure and delivery rate versus time curve for the drug contained in the ampule. The pressure of the drug within the ampule can be given an initial high pressure spike at the start of the delivery. The altered pressure curve can provide enhanced transcutaneous drug penetration, less pain, and more patient comfort. The enclosed container needleless injector 5 can be placed onto the cutaneous tissue of the patient. The orifice 290 of the disposable ampule 245 can be placed in direct contact with the cutaneous tissue or a gap can be placed between the cutaneous tissue and the orifice 290.

The enclosed container needleless injector 5 has been activated to form an unloaded state as shown in FIG. 5B. The ampule has been removed following activation of the enclosed container needleless injector 5 as shown in FIG. 5C. Activation has been accomplished by pushing down on the trigger 480 or an activation means causing the trigger pin 475 to push the retainer 450 downward allowing the latching balls 445 to enter the retainer recess 455 and unlatch the ram 425. The enclosed container 370 undergoes an expansion from the smaller enclosed container loaded volume 375 to the larger enclosed container unloaded volume 380. The loading force acting on the movable surface 520 by the working gas 160 acts to push the ram head 435 against the ampule piston 270 and discharge the drug contained in the ampule volume 280 out of the orifice 290. The movable surface 520 is understood to interface with the disposable ampule 245. The trigger spring 500 returns the trigger 480 to the position found in FIG. 5A. It is understood that other mechanical trigger mechanisms or activation means can be used to activate the needleless injector and allow the compressed working gas 160 to expand.

The fill valve 135 located at the top of the upper bellows housing end plate 360 provides an access site with a static seal through which the working gas 160 can be added or removed. The fill valve 135 has the same structure and reference numeral as that shown in FIGS. 1A and 1B. The fill valve 135 is not required by the present invention and can be eliminated or capped off. Adding working gas 160 to the enclosed container 370 can alter the spring constant and the spring rate of the enclosed container 370 and the enclosed container power supply 515. Increasing the amount of working gas 160 in the enclosed container unloaded volume 380 and hence increasing the unloaded pressure has the effect of increasing proportionately the spring constant and increasing proportionately the spring rate. The working gas 160 exerts a force onto a movable surface area 530 of the movable surface 520 in an unloaded state equal to the multiplication product of the movable surface area 530 and the unloaded pressure. Increasing the movable surface area 530 will increase proportionately both the spring constant and the spring rate of the enclosed container 370. Increasing the enclosed container unloaded volume 380 while maintaining the movable surface area 530 constant results a proportional reduction in the spring rate and the spring constant for the enclosed container 370 remains constant. Increasing the enclosed container unloaded volume 380 and the movable surface area 530 the same percentage results in a proportional increase in the spring constant and the spring rate remains constant.

Changing the movable surface area 530, the enclosed container unloaded volume 380, or the unloaded pressure within the enclosed container 370 therefore allows the spring rate and spring constant to be altered independently. The enclosed container power supply 515 of the present invention can be designed to provide a great variety of enclosed container pressure versus enclose container volume curves in going from the loaded to the unloaded state. The enclosed container power supply 515 of the present invention can therefore be matched closely to a specific application. The enclosed container needleless injector of FIGS. 5A and 5B provides a thin pencil-like device that is easily carried by the patient to a remote site out of the home to perform and injection. An enclose container length 535 extends from the upper bellows housing endplate 360 to the ram plate 365. A stroke length 537 can be adjusted to deliver the appropriate volume of drug at an appropriate pressure and rate to the patient. It is understood that the bellows 340 of FIGS. 5A and 5B with a large enclosed container length 535 for its enclosed container unloaded volume 380 can be constructed within the teachings of this disclosure with a relatively short enclosed container length 535 an a much larger movable surface area 530. Similarly, the enclosed container 45 of FIGS. 1A and 1B can be constructed with a longer enclosed container length 315 (see FIG. 2C) and a smaller movable surface area 175 (see FIG. 1A). FIG. 5C shows the enclosed container needleless injector 5 of the present invention with an enclosed container unloaded volume 380 indicative of the unloaded state without any thing seated in the receiver head 420. The enclosed container needleless injector 5 and the enclosed container power supply 335 of the present invention are intended to be reusable; alternately, they can provide a one time use and be disposable. The enclosed container power supply 335 can be provided in a loaded or unloaded state and can be discarded following expansion of the working gas 160. The components of the enclosed container needleless injector 5 that would be required to interface with a disposable enclosed container power supply 335 could be reduced in number. A disposable enclosed container power supply 335 may not require interface with a reset means and may not require relatching since it is only used once.

Figure 6:
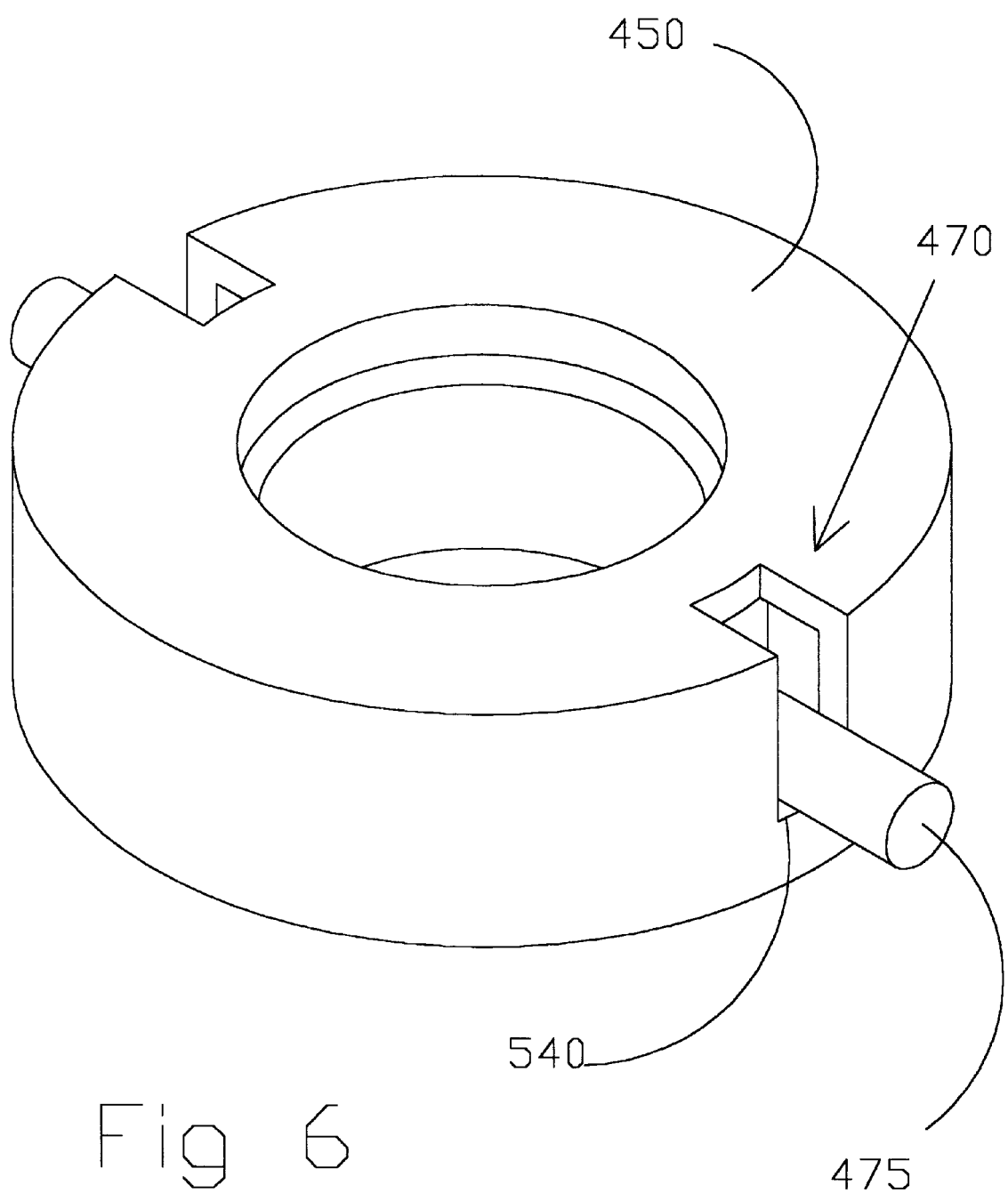
FIG. 6 is a partially sectioned view of a retainer and trigger pin for an enclosed container needleless injector with a bellows.
Figure 7A:
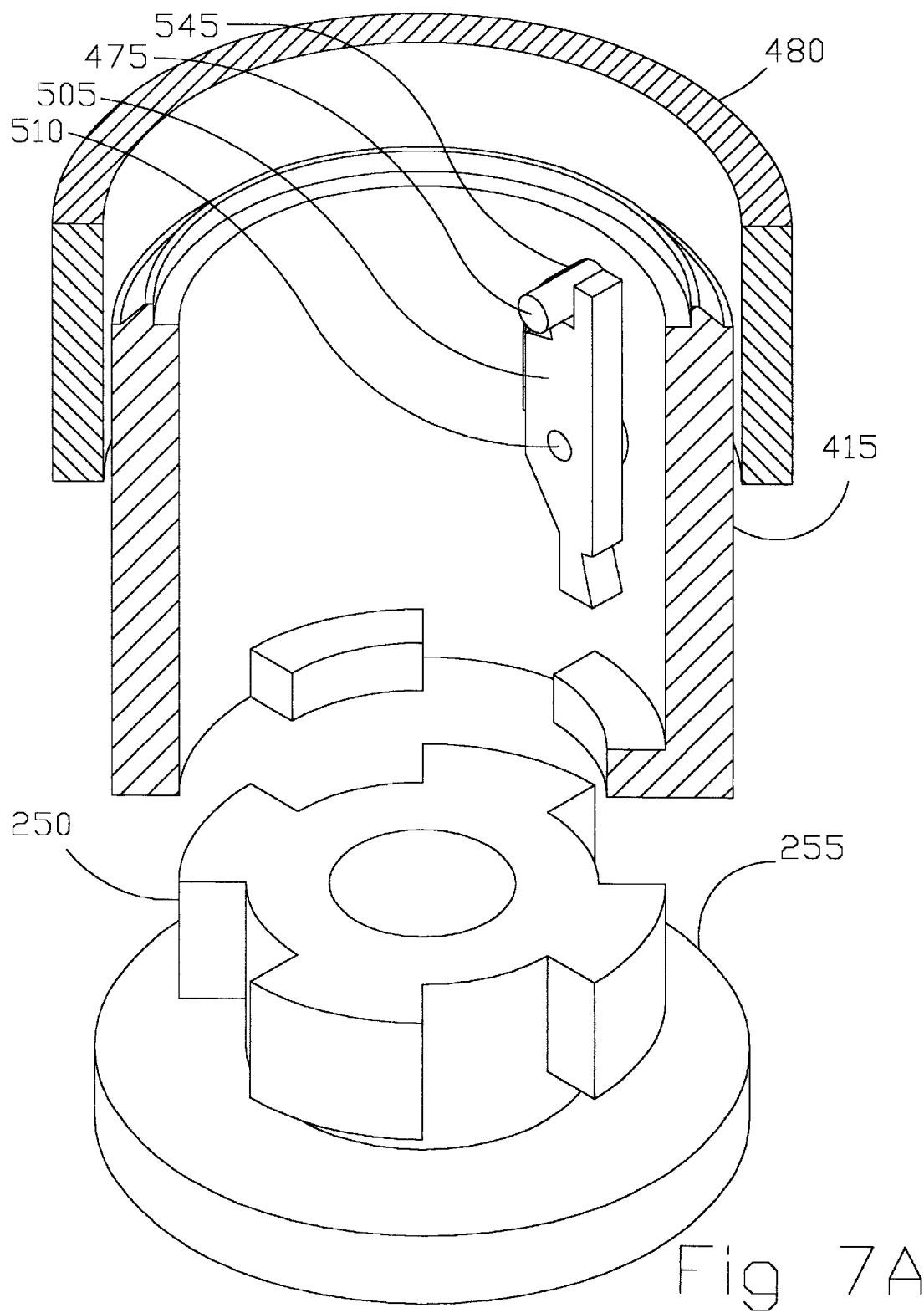
FIG. 7A is a partially sectioned view of a portion of an enclosed container needleless injector with a bellows showing a safety link in a locked position.
Figure 7B:
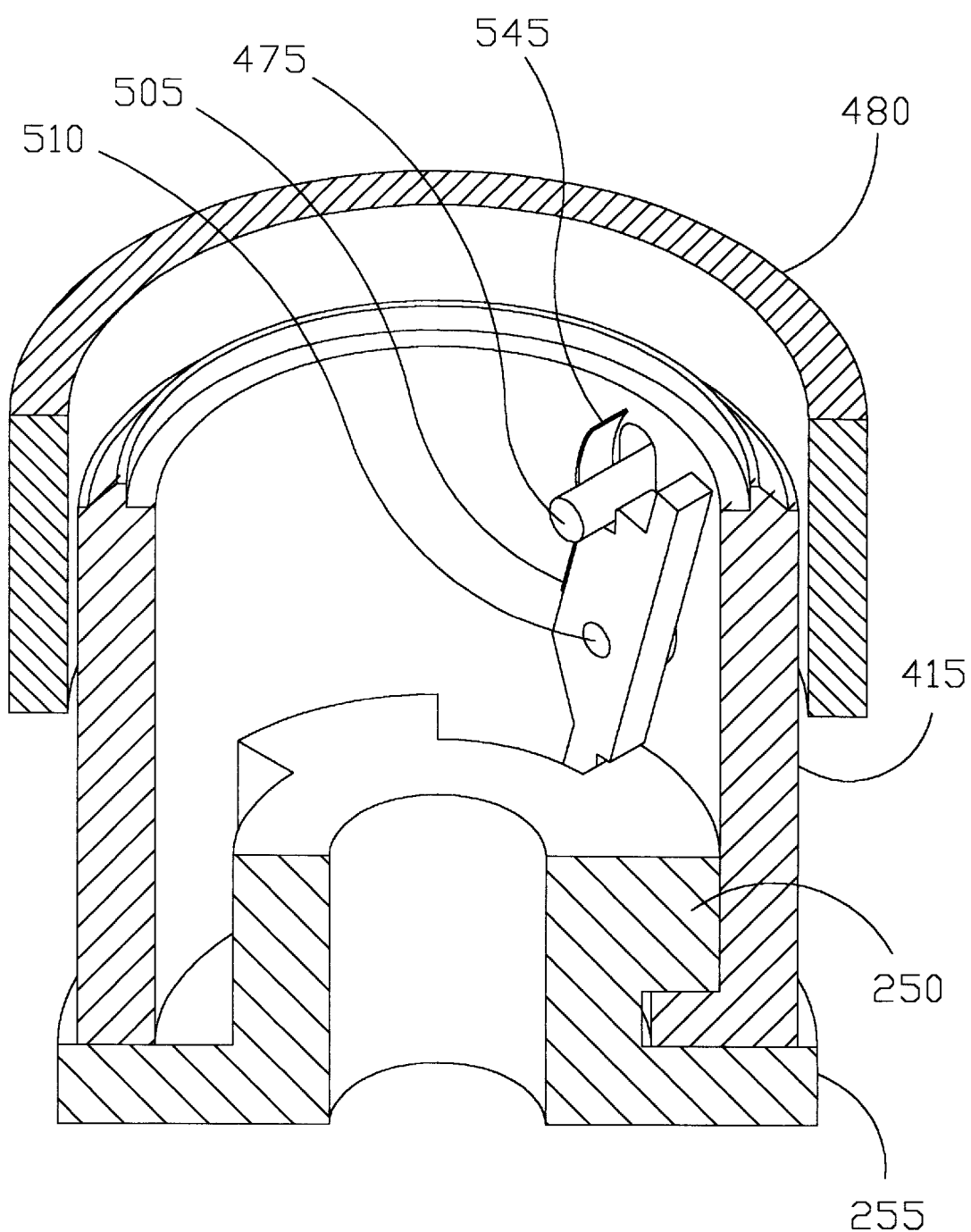
FIG. 7B is a partially sectioned view of a portion of an enclosed container needleless injector with a bellows showing a safety link in an unlocked position.

FIG. 6 is a partially sectioned view of the retainer 450 and trigger pin 475. The retainer slot lower edge 540 of the retainer slot 470 is in contact with the trigger pin 475 as shown in FIG. 5A. FIGS. 7A and 7B show a partially sectioned view of the safety link 505 for the enclosed container needleless injector 5 shown in FIGS. 5A and 5B. The safety link 505 prevents the trigger 480 from being activated if an ampule housing 255 is not seated in the receiver 415. In FIG. 7A the safety link 505 prevents movement of the trigger pin 475 downward. A safety spring 545 maintains the safety link 505 in a safety position. In FIG. 7B the safety link 505 rotates about a safety link pivot 510 with an ampule housing 255 seated onto the receiver 415. The trigger pin 475 is able to move downward to activate the enclosed container needleless injector 5 (see FIGS. 5A and 5B).

The shape of the bellows used in the power supply of this invention does not have to be cylindrical in shape. The bellows can be spherical or any other shape as long as it forms a portion of an enclosed container that can change in volume and does not have any active seals. Similarly, the diaphragm used in the power supply of this invention can take on any shape as long as it forms a portion of an enclosed container that can change in volume and does not have any active seals. The power supply of the present invention does not require that the enclosed container contain a bellows or a diaphragm. The invention only requires that the power supply include as its major power source an enclosed container that is capable of changing in volume and that the enclosed container does not have any active seals.

Figure 8A:
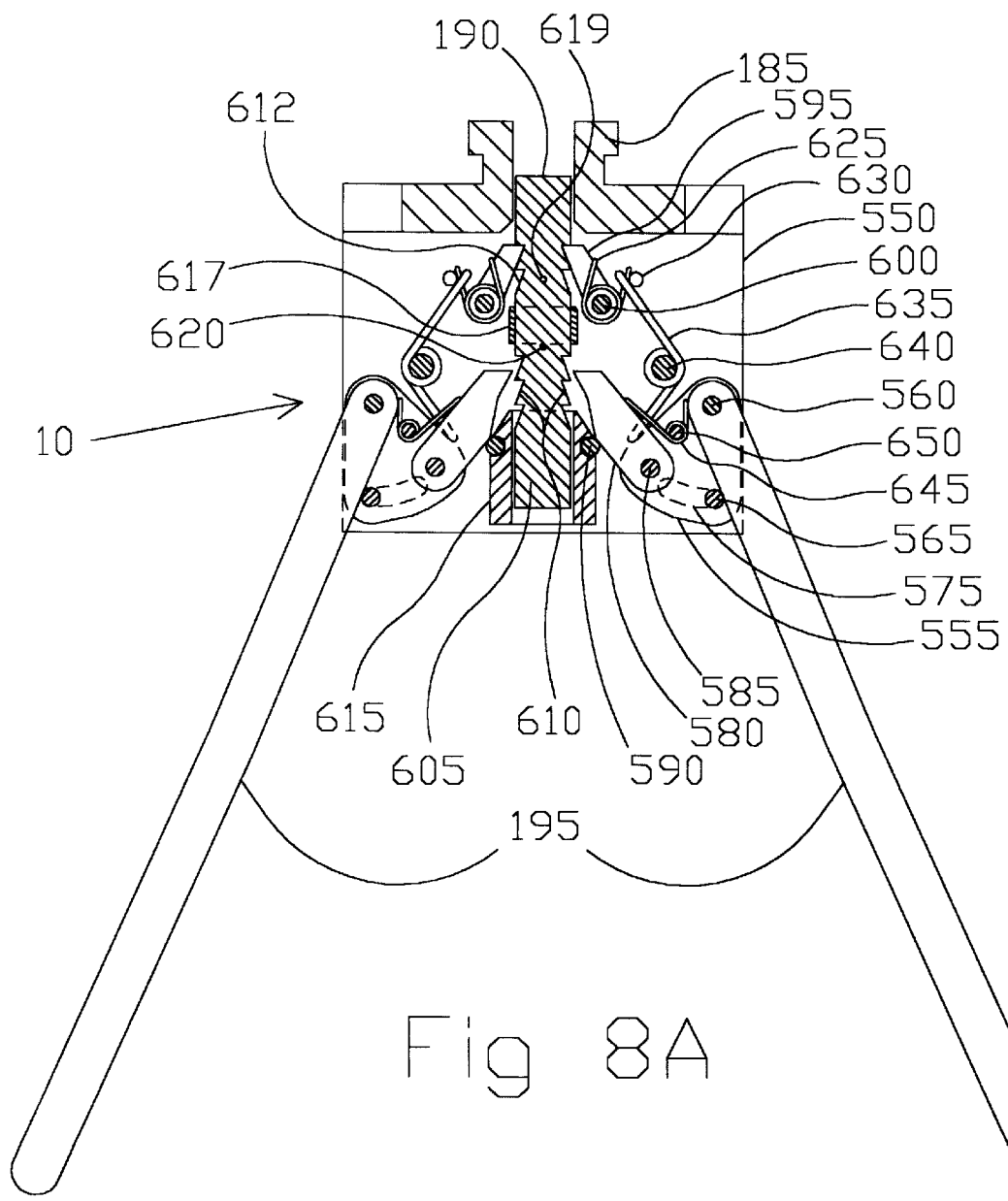
FIG. 8A is a partially sectioned view of a remote reset mechanism ready for seating with an enclosed container needleless injector.

FIG. 8A is a partially sectioned view of the remote reset mechanism 10 shown in FIGS. 1A and 1B. A reset housing 550 has a reset head 185 that is configured to seat with a receiver head 80 & 420 of an enclosed container needleless injector 5 (see FIG. 1A). Two reset handles 195 are each attached to reset levers 555 and pivot about reset handle pivots 560. Reference numerals are intended to refer to all like components with like functions. Two reset handle stops 565 attached to reset levers serve to stop each of the reset handles 195. The reset handle stops 565 attached to the reset levers 555 are positioned in reset housing slots 575. Two reset pushing latches 580 are pivotally connected to reset levers 555 with reset pushing latch pivots 585. Two reset pushing latch stops 590 attached to the reset housing 550 serve to disengage the reset pushing latches 580 during the reset of the reset pusher head 190 downwards prior to the next use of the remote reset mechanism 10. Two reset holding latches 595 are pivotally connected to the reset housing 550 with reset holding latch pivots 600. A reset pusher 605 with a reset pusher head 190 and two ratchet pushing sets 610 and two ratchet holding sets 612 is slidingly held to the reset housing 550 with a reset pusher bushing 615. A reset pusher slide 617 is slidingly fit over the reset pusher 605 between top 619 and bottom 620 reset pusher stops which are attached to the reset pusher 605. Holding latch springs 625 are secured by holding latch spring stops 630 and pivot around reset holding latch pivots 600 to apply spring force to reset holding latches 595. Reset lever springs 635 pivot about reset lever spring pivots 640 to apply a spring force to reset levers 555. Pushing latch springs 645 pivot about pushing latch spring pivots 650 to apply a spring force to reset pushing latches 580.

Movement of the reset handles 195 inward toward each other generates rotation of the reset levers 555 through a small angle determined by movement of the reset levers 555 along the reset housing slots 575. Rotation of the reset levers 555 causes the reset pushing latches 580 to engage the ratchet pushing sets 610 and push the reset pusher 605 upwards. The reset holding latches 595 engage the ratchet holding sets 612 and hold the reset pusher 605 from moving downward. The reset pushing latches 580 are retracted downward so as to engage the ratchet sets 610 at a lower position along the reset pusher 605. This is accomplished by moving the reset handles 195 outward away from each other causing the reset levers 555 to rotate and cause the reset pushing latches 580 to move downwards. Repeating the inward and outward motion of the reset handles 195 causes the reset pusher head 190 to move upward.

Figure 8B:
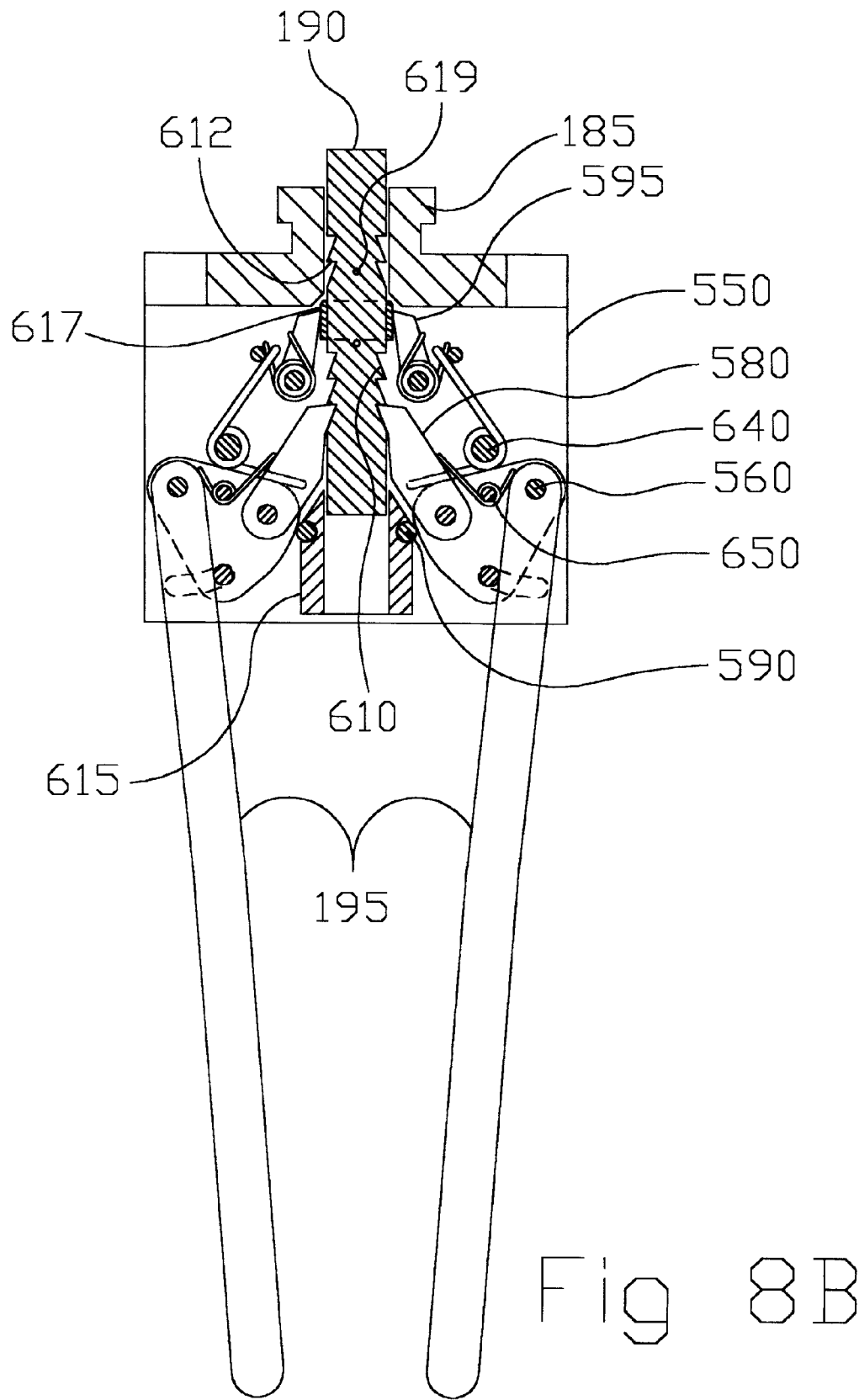
FIG. 8B is a partially sectioned view of a remote reset mechanism following resetting of an enclosed container needleless injector.

With the remote reset mechanism 10 interfacing with the enclosed container needleless injector 5, the reset pusher head 190 comes into direct contact with the ram head 70 & 435 and pushes the ram head 70 & 435 and the movable surface 175 & 520 into a loaded position as described in FIGS. 1B and 5A. With the movable surface 175 and 520 in a loaded position and the latch mechanism 205 and 525 holding the movable surface 175 and 520 from any further movement, the remote reset mechanism 10, can then be removed. During the last draw movement of the reset handles 195 together, the bottom reset pusher stop 620 contacts the reset pusher slide 617 driving it upwards in between reset holding latches 595 and holding reset holding latches 595 out of contact with ratchet holding sets 612 as shown in FIG. 8B. Thus, following the latching of the enclosed container needleless injector 5, the reset holding latches 595 of the remote reset mechanism 10 are automatically held apart from the ratchet holding sets 612 and with the reset handles 195 apart and the reset pushing latches 580 disengaged from the ratchet pushing sets 610 allowing the remote reset mechanism 10 to be removed from the needleless injector 5.

The reset pusher head 190 can be pushed flush with the reset head 185 by applying a digital force. The remote reset mechanism 10 is ready to be used to reset another enclosed container needleless injector 5 that requires resetting. The ram head 70 and 435 of the enclosed container needleless injector 5 is placed into contact with the reset pusher head 190 as the remote reset mechanism 10 is seated with the enclosed container needleless injector 5. The ram head 70 and 435 pushes the reset pusher head 190 downward until the top pusher stop 619 contacts the reset pusher slide 617 pushing it down and out of contact with the reset holding latches 595. The remote reset mechanism 10 is ready to reset the enclosed container needleless injector 5 as described earlier. The presence of the reset pusher slide 617 allows the one way ratcheting action of the reset holding latches to be automatically released so that the remote reset mechanism can be easily removed from the enclosed container needleless injector 5.

This hand operated remote reset mechanism 10 could also have been designed to operate by electromechanical or hydraulic means. Furthermore, it is understood that the enclosed container power supply 165 & 515 and the enclosed container needleless injector 5 described in this disclosure can also contain a reset means as a component of the needleless injector device rather than being remote. It is also understood that the remote reset mechanism 10 could also be used with other needleless injectors described earlier in the prior art section of this disclosure.

Figure 8C:
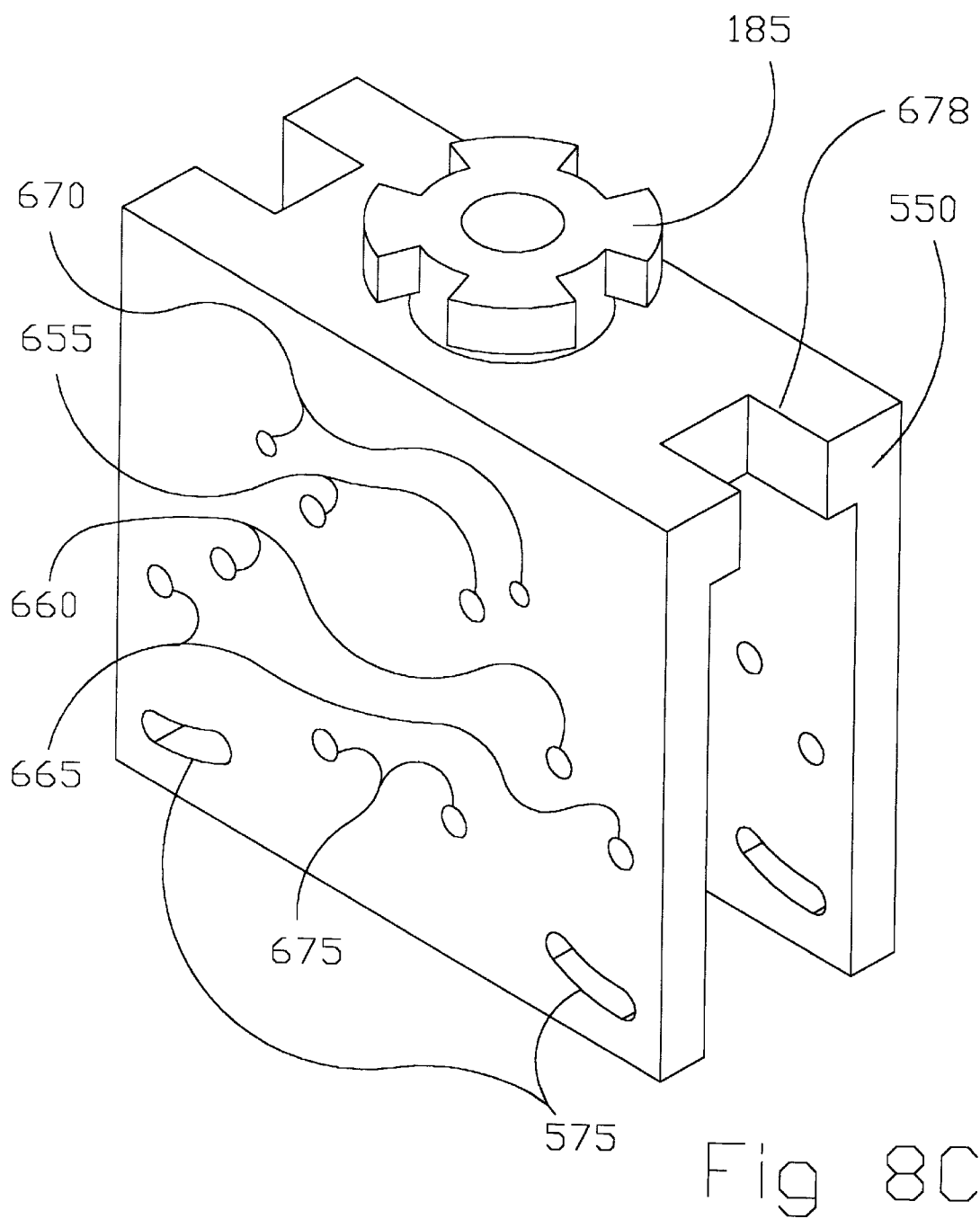
FIG. 8C is an isometric view of a reset housing.
Figure 8D:
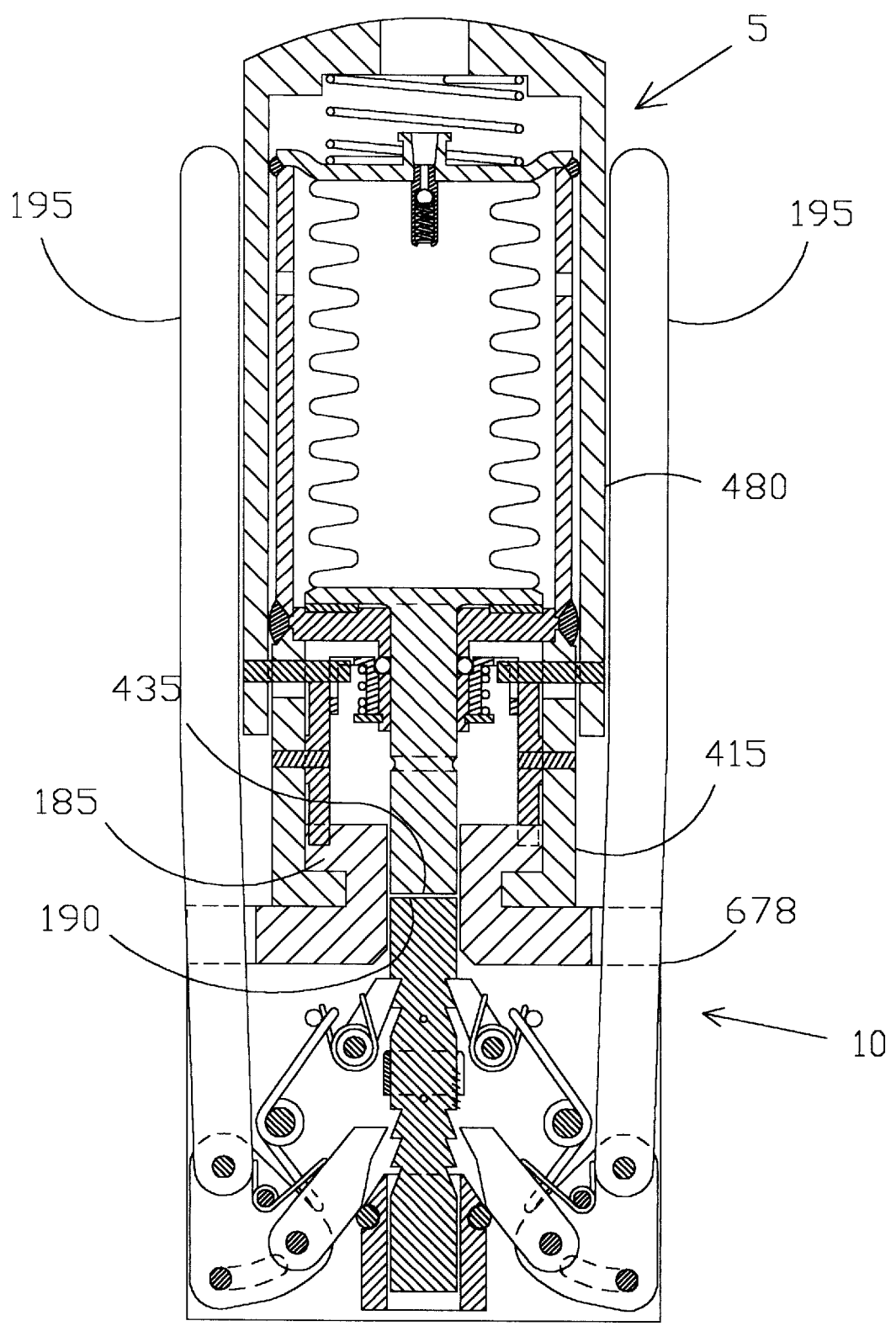
FIG. 8D is a partially sectioned view of an enclosed container needleless injector in an unloaded state with a bellows and seated with a remote reset mechanism.

FIG. 8C is an isometric view of the reset housing 550 of FIGS. 8A and 8B showing the reset head 185 and the reset housing slots 575. Additionally are shown sites for pins that serve as stops and pivots as shown in FIGS. 8A and 8B. Sites that hold pins for the purpose of pivoting include reset holding latch pivot sites 655, reset lever spring pivot sites 660, and reset handle pivot sites 665. Sites that hold pins for the purpose of providing a stop include holding latch spring stop sites 670, and reset pushing latch stop sites 675. Two handle reliefs 678 are located on the reset housing to provide a seat for reset handles 195 as they are folded back against the reset housing 550 during storage as shown in FIG. 8D. FIG. 8D shows the enclosed container needleless injector 5 seated with the remote reset mechanism 10. The reset pusher head 190 is shown in contact with ram head 435. The reset handles 195 have been rotated such that they are aligned adjacent to the trigger 480 and are seated in handle reliefs 678. This position for the reset handles 195 form an efficient and compact package for carrying or storing the enclosed container needleless injector 5 along with the remote reset mechanism 10.

Other embodiments of the present invention include a two-stage needleless injector having an enclosed container that is capable of changing in volume without any active seals. The volume change that occurs during activation of the needleless injector occurs in two stages. In the first stage a movable surface with a larger surface area interfaces with the piston of a drug ampule to impart a larger force than in the second stage where a movable surface with a smaller surface area interfaces with the piston of a drug ampule to impart a smaller force. The first stage involves a first volume change with a first pressure change at a higher average pressure that generates a higher velocity jet of the drug to allow for better penetration into the cutaneous tissue. A second stage involves a second volume change with a second pressure change at a lower average pressure, and with a stepped change in pressure between the first and second stages, and a stepped change to a lower jet velocity to deliver a substantial amount of the drug to the patient with a lower velocity jet. The benefits of this two-stage drug delivery can include a more efficient drug penetration through the skin and a more comfortable and effective drug delivery with less pain to the patient. It is further understood that a three-stage needleless injector can similarly be used to deliver a drug with three separate pressure changes, each pressure change involving a stepped change in pressure and being associated with a stepped change in jet velocity. The two- or three- stage needleless injector can be constructed using a diaphragm design or a bellows design as described in the earlier embodiments.

Figure 9A:
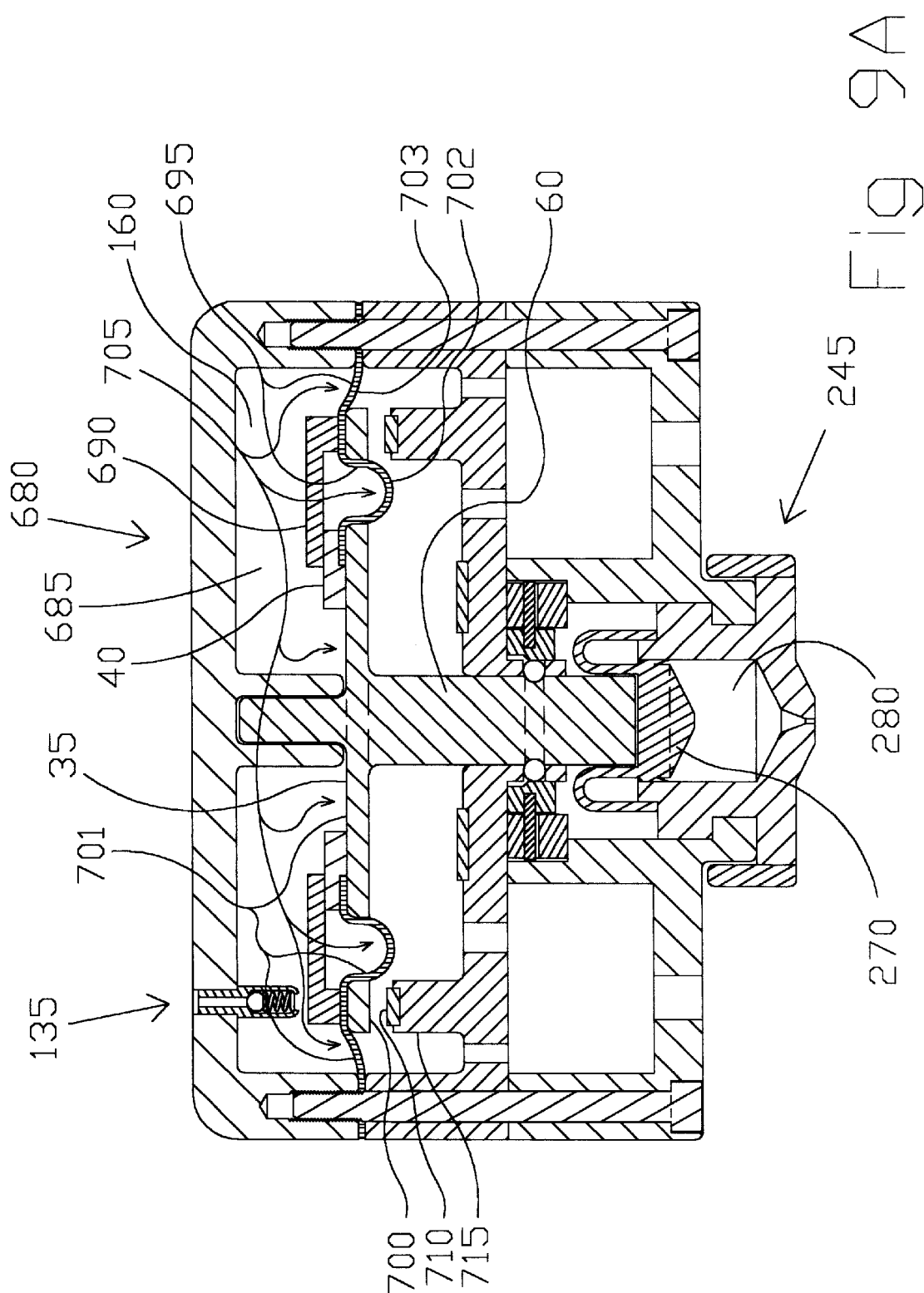
FIG. 9A is a partially sectioned view of a two-stage enclosed container needleless injector with diaphragm in a loaded state and seated with a disposable ampule.

An embodiment of a two-stage enclosed container needleless injector 680 of the present invention with a diaphragm is shown seated to disposable ampule 245 in FIGS. 9A and 9B. FIG. 9A shows the two-stage enclosed container needleless injector 680 in a loaded state with enclosed container loaded volume 685. An intermediate diaphragm ring 690 is attached to diaphragm means 695 which is attached to an intermediate diaphragm stop 700. The diaphragm means can be formed from two or more diaphragm sections that are either contiguously adjoined or the sections can be separate and distinct. In the loaded state the intermediate diaphragm ring 690 is in contact with the clamp ring 40 but it is not required to form a seal with the clamp ring 40. Pressure of the working gas 160 is acting upon a larger first stage movable surface 701 comprising the diaphragm end plate 35, clamp ring 40, inner diaphragm section 702, and outer diaphragm section 703 with a first stage movable surface area 705 comprising the area of contact of the first stage movable surface 701 with the working gas 160. The first stage movable surface 701 moves downward during the first stage of volume change upon activation of the enclosed container needleless injector 680. The force applied by the pressure in the working gas 160 on the larger first stage movable surface area 705 generates a larger force that is transmitted through the ram 60 to the ampule piston 270 of the disposable ampule 245. The intermediate diaphragm stop 700 is forced into contact with a lower diaphragm housing ring stop 710 that is attached to a lower diaphragm housing ring 715 as the two-stage enclosed container needleless injector 680 undergoes the first stage of volume expansion from the enclosed container loaded volume 685 and reaches an enclosed container intermediate volume 720 as shown in FIG. 9B. The two-stage enclosed container needleless injector 680 quickly passes through the intermediate state shown in FIG. 9B and continues on to the unloaded state shown in FIG. 9C. The space between the outer diaphragm section 703 and the lower diaphragm housing 723 can be vented from lower diaphragm housing outer vent 725 into the enclosed container outside space 48.

Figure 9C:
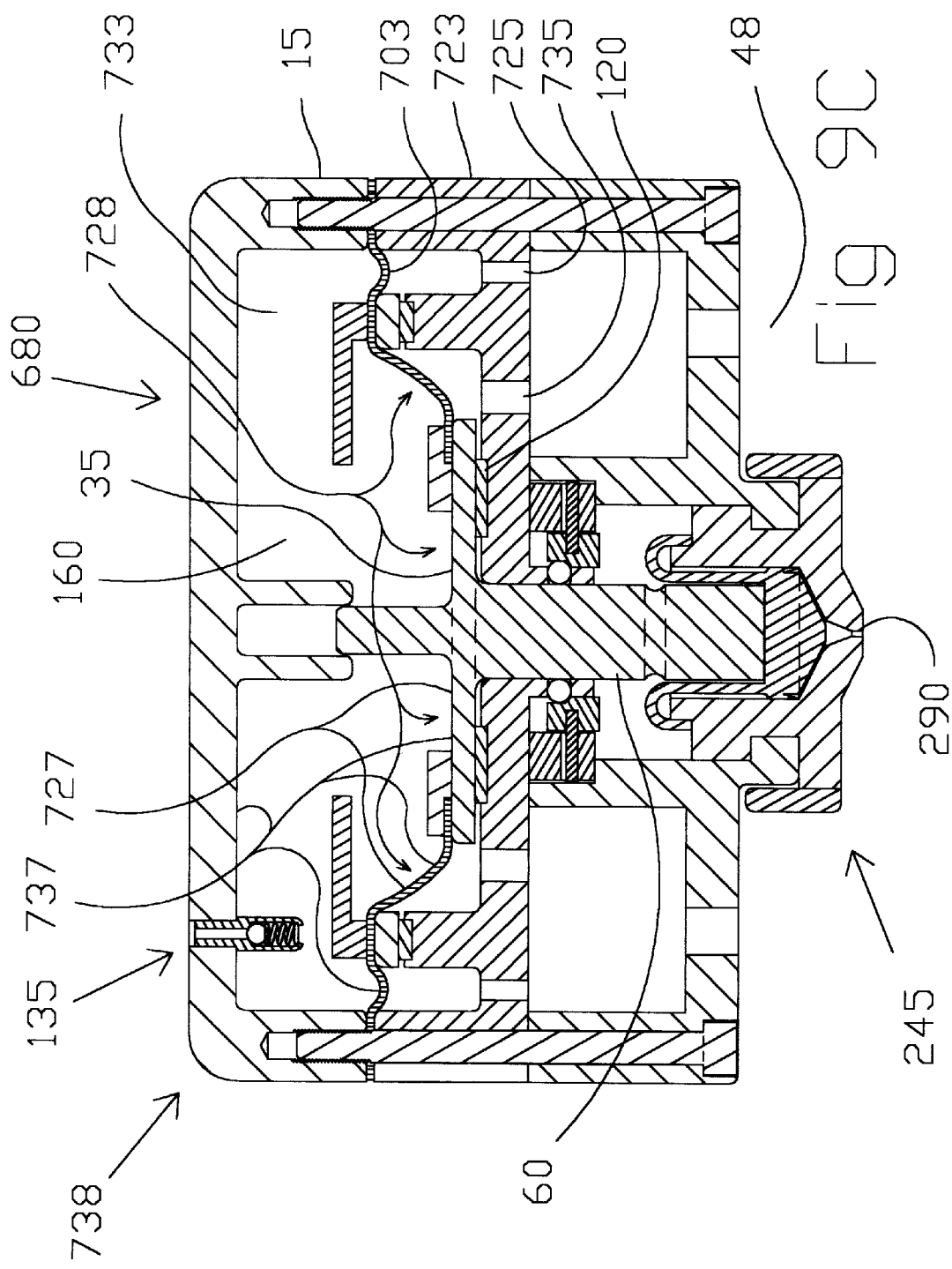
FIG. 9C is a partially sectioned view of a two-stage enclosed container needleless injector with diaphragm in an unloaded state and seated with a disposable ampule.

In the second stage, working gas 160 can now only apply pressure to a second stage movable surface 727 comprising the diaphragm end plate 35, the clamp ring 40 and the inner diaphragm section 702 with a smaller second stage movable surface area. 728 in contact with working gas 160. The first stage 701 and second stage 727 movable surface interfaces through the ram 60 with the latch mechanism 525, the disposable ampule 245, and the remote reset mechanism (see FIGS. 1–9). The applied pressure of working gas 160 on the second stage movable surface area 728 drives the diaphragm end plate 35 into contact with the bumper stop 120 and achieving an enclosed container unloaded volume 733 as shown in FIG. 9C. Inner diaphragm section 702 and outer diaphragm section 703 can be a single diaphragm with two contiguous portions or sections or they can be two separate diaphragms or diaphragm sections. The space between the inner diaphragm section 702 and the lower diaphragm housing 723 can be vented from the lower diaphragm housing inner vent 735 into the enclosed container outside space 48. The enclosed container 737 for this embodiment includes the components whose surface areas form the first stage movable area 705, the second stage movable area 728, and the upper diaphragm housing 15. An enclosed container surface formed by the components of the enclosed container 737 forms a continuous surface that is in contact with working gas 160 and does not contain any active seals. The first stage movable surface 701 forms a portion and the second stage movable surface 727 forms a portion of the enclosed container surface. The enclosed container power supply 738 for this embodiment includes the components of the enclosed container 737 plus the ram 60 and the working gas 160.

This two-stage enclosed container needleless injector 680 causes the diaphragm end plate to encounter a stepped change in force at an intermediate point during the volume change or expansion from the enclosed container loaded volume 685 to the enclosed container unloaded volume 733. The force applied by the pressure in the working gas 160 on the smaller second stage movable surface area 728 generates a stepped change smaller force that is transmitted via the ram 60 to the ampule piston 270 of the disposable ampule 245. A stepped change in force is applied to the movable surface area at the intermediate state shown in FIG. 9B. Due to a change in the movable surface area over which the pressure of the working gas 160 is being applied, this stepped change in force is transferred through the ram 60 and to the ampule piston 270. The result is a stepped change in pressure found in the drug contained within an ampule intermediate volume 739. This stepped change in pressure within the ampule intermediate volume 739 causes the drug contained in the disposable ampule 245 to undergo a stepped change in velocity as the drug exits the orifice 290. The result is an initial high velocity stream of drug during the first stage to help provide better penetration of the drug through the cutaneous tissue followed by a lower velocity stream of drug during the second stage to deliver the appropriate amount of drug to the patient with more comfort. All other reference numerals indicated in FIGS. 9A–9C correspond to those elements previously or otherwise described.

Figure 10A:
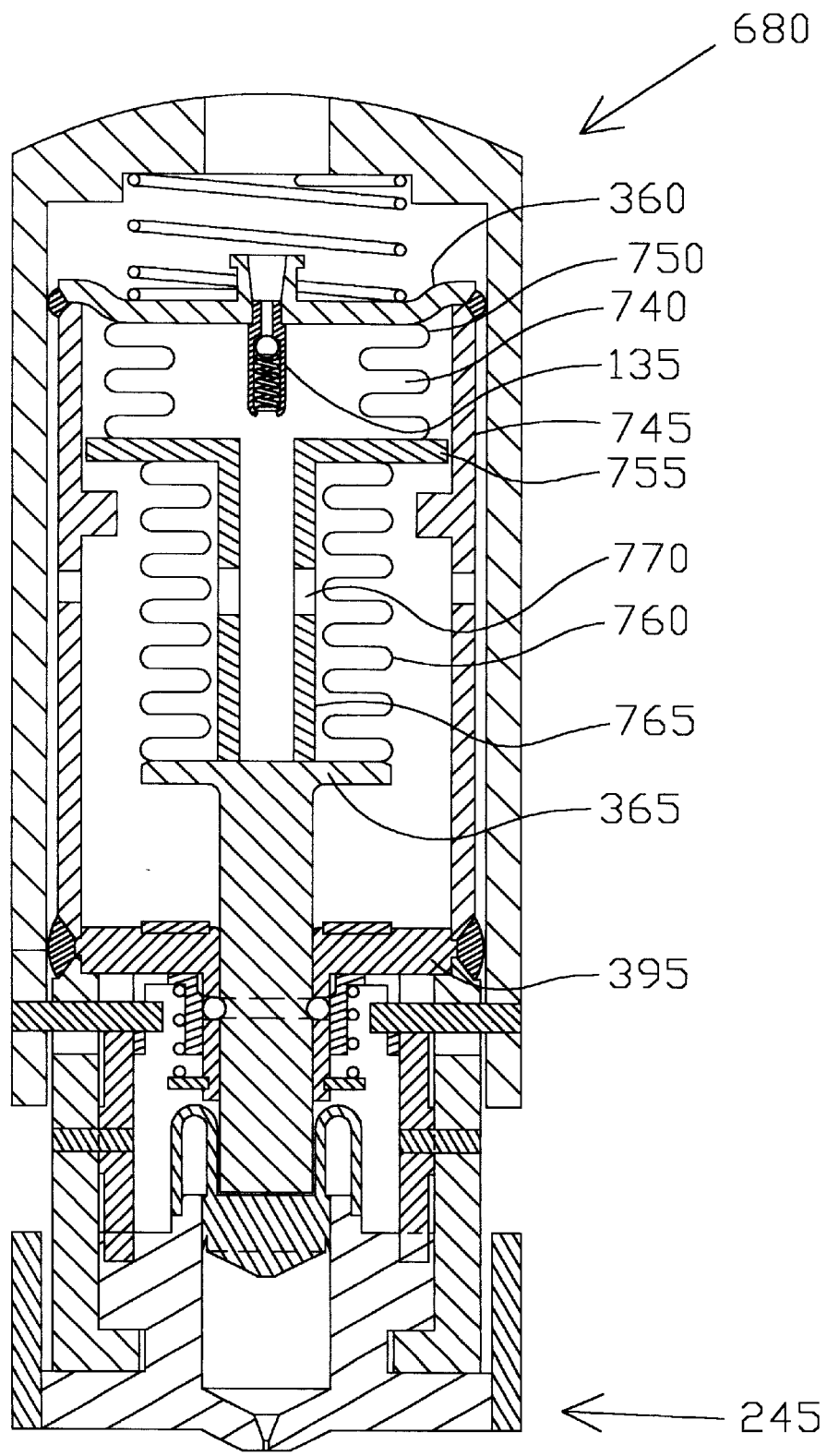
FIG. 10A is a partially sectioned view of a two-stage enclosed container needleless injector with bellows in a loaded state and seated with a disposable ampule.
Figure 10B:
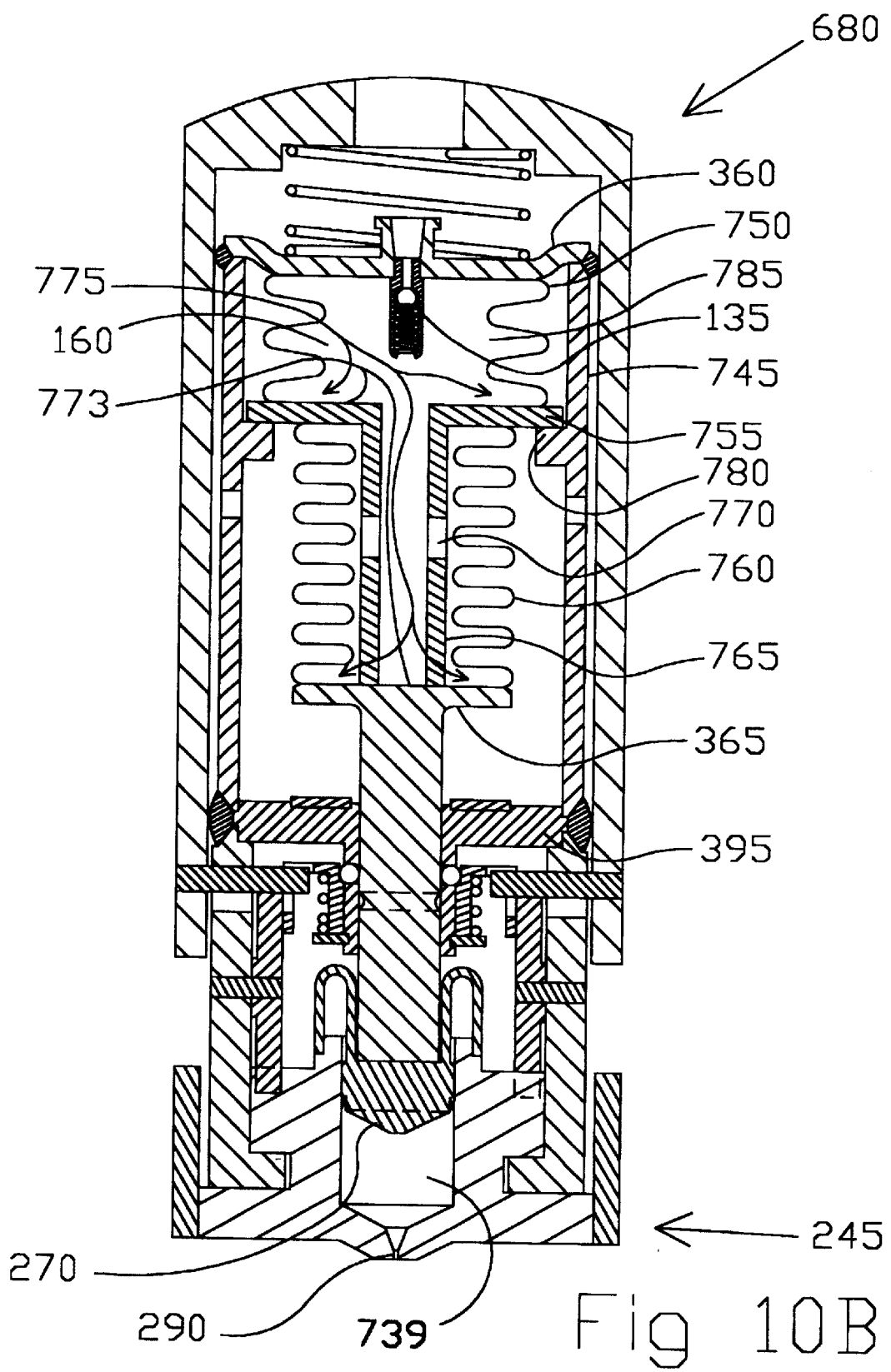
FIG. 10B is a partially sectioned view of a two-stage enclosed container needleless injector with bellows in an intermediate state and seated with a disposable ampule.

Another embodiment of a two-stage enclosed container needleless injector 680 with a bellows is shown seated to a disposable ampule 245 in FIGS. 10A–10B. FIG. 10A shows the two-stage enclosed container needleless injector 680 in a loaded state with an enclosed container loaded volume 740. A bellows housing 745 attaches to an upper bellows housing end plate 360 and a lower bellows housing end plate 395. A first bellows 750 is attached to the upper bellows housing end plate 360 and is attached to an intermediate connector plate 755. A second bellows 760 is attached to the intermediate connector plate 755 and to the ran plate 365. The first and second bellows can be formed from one contiguous bellows with a step change in cross sectional area or shape. It is further understood that three bellows can be assembled in a manner similar to that shown to provide three different movable surface areas for the movable surface. An intermediate connector tube 765 which is connected to the intermediate connector plate 755 has an intermediate connector vent 770 and is in contact with the ram plate 365 in the loaded state as shown in FIG. 10A. It is further understood that a bellows means can be identified to include the first bellows 750, the second bellows 760, plus components sealingly attached to the first 750 and second 760 bellows including the ram plate 365, and intermediate connector plate 755 which move during expansion and compression of the working gas 160.

During activation of the two-stage enclosed container needleless injector 680 the pressure of the working gas 160 acts upon the larger first stage movable surface 773 comprising the intermediate connector plate 755 and the ram plate 365. The first stage movable surface area 775 comprises the area of contact of working gas 160 with the first stage movable surface 773. Pressure from the working gas 160 upon the first stage movable surface area 775 creates a larger force on these elements and causes these elements to move downward until the intermediate connector plate 755 comes into contact with a bellows housing intermediate stop 780 attached to the bellows housing 745 as shown in FIG. 10B. The working gas 160 has expanded in volume to occupy an enclosed container intermediate volume 785 and the working gas 160 can move freely through the intermediate connector vent 770. The force applied to the ram plate 365 and intermediate connector plate 775 is transferred to the ram 425 during the first stage generating a larger force on the ampule piston 270. This larger force is larger than a smaller force generated during the second stage. This larger force generated during the first stage causes a high pressure to be formed in the drug contained in the disposable ampule volume 280 resulting in flow of the drug contained in the ampule volume 280 through the orifice 290 at a high velocity. This high velocity stream of drug is well suited to penetrate through the outer tissue of skin or cutaneous tissue. Due to contact of the intermediate connector plate 775 with the bellows housing intermediate stop 780, the first bellows can no longer expand beyond the intermediate state shown in FIG. 10B.

Figure 10C:
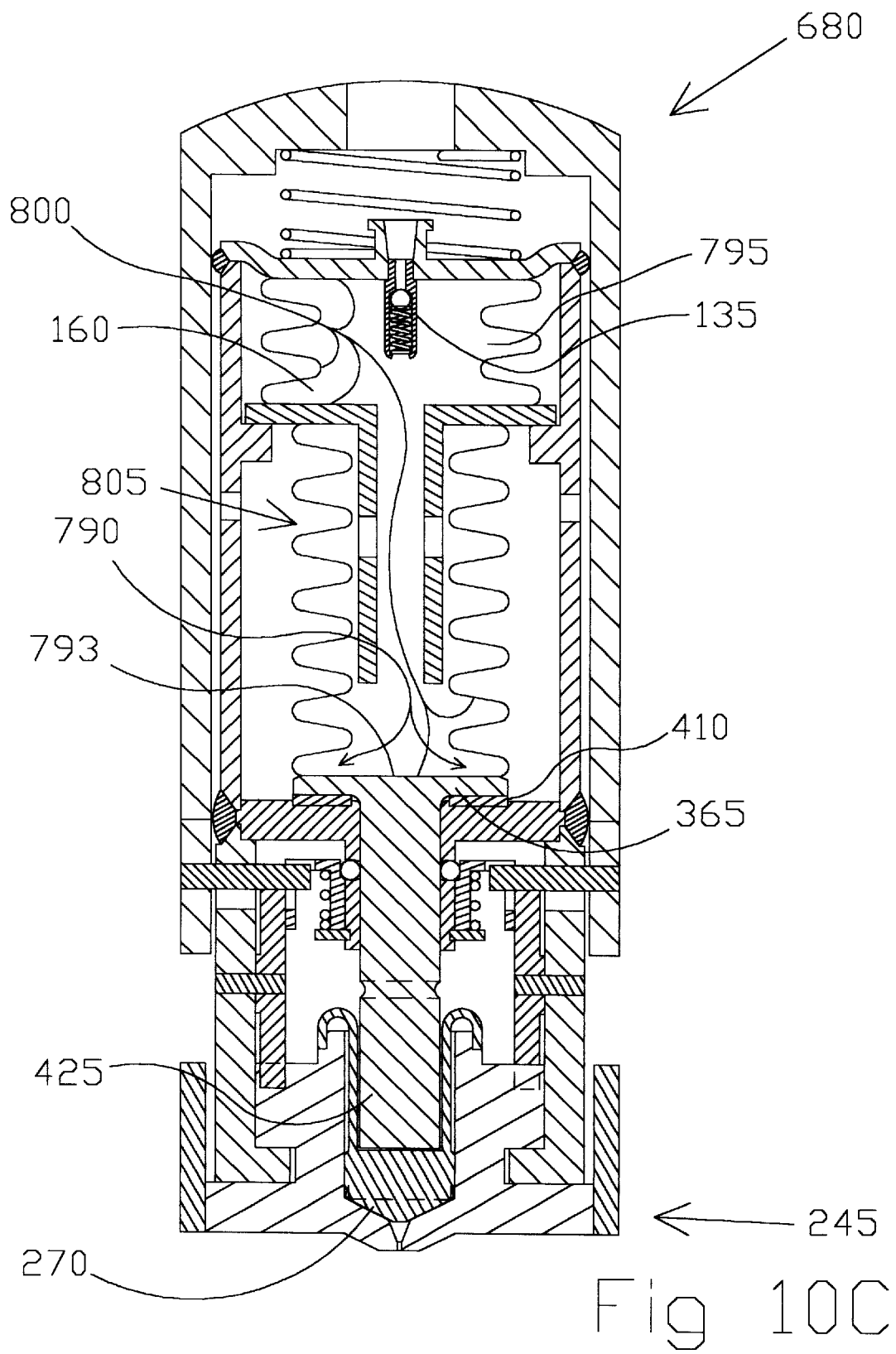
FIG. 10C is a partially sectioned view of a two-stage enclosed container needleless injector with bellows in an unloaded state and seated with a disposable ampule.

The pressure of the working gas 160 then acts upon the smaller second stage movable surface area 790 of the second stage movable surface 793 comprising the ram end plate 365 to force it downwards into contact with bumper stop 410 and forming an enclosed container unloaded volume 795 as shown in FIG. 10C. This second stage expansion of the working gas generates a stepped reduction in force upon the ram end plate due to the reduction in surface area over which the pressure of the working gas is applied. This reduced force acting on the ram plate 365 causes less force to be transmitted through the ram 425 to the ampule piston 270 and a stepped change to a lower pressure being generated in the ampule intermediate volume 739 during the second stage of working gas 160 volume expansion. The drug contained in the ampule intermediate volume 739 is then delivered during the second stage to the patient as a lower velocity stream with more control in delivery volume and more comfort to the patient. All other reference numerals indicated in FIGS. 10A–10C correspond to those elements previously or otherwise described. The enclosed container 800 of this embodiment includes the upper bellows housing end plate 360, the first bellows 750, the intermediate connector plate 755, the second bellows 760, and the ram plate 365. An enclosed container surface is a continuous surface formed by the components of the enclosed container 800 and does not contain an active seal. The first stage movable surface 773 forms a portion and the second stage movable surface 793 forms a portion of the enclosed container surface. The enclosed container power supply 805 of the present embodiment comprises the enclosed container 800 plus the ram 425 and the working gas 160 contained within the enclosed container 800. The first stage 773 and second stage 793 movable surface interface with the ram 425, the latch mechanism 525, the disposable ampule 245, and the remote reset mechanism (see FIGS. 5–10).

The two-stage enclosed container needleless injector shown in FIGS. 9A–9C and 10A–10C can be reset using a reset mechanism such as the remote reset mechanism 10. The working gas 160 is compressed from the enclosed container unloaded volume 795 and 733 back to the enclosed container loaded volume 740 and 685. It is understood that these embodiments can also contain the fill valve 135 as shown and described previously.

REFERENCE NUMERALS IN DRAWINGS

5 Enclosed Container Needleless Injector
10 Remote Reset Mechanism
15 Upper Diaphragm Housing
20 Lower Diaphragm Housing
25 Bolts
30 Diaphragm 35 Diaphragm End Plate
40 Clamp Ring
45 Enclosed Container
47 Enclosed Container Inside Space
48 Enclosed Container Outside Space
50 Guide Pin
55 Guide
60 Ram
65 Latch Groove
70 Ram Head
75 Receiver
80 Receiver Head
85 Latch Ball Holes
90 Latch Balls
95 Retainer
100 Retainer Recess
105 Trigger Pin
110 Trigger
115 Trigger Slot
120 Bumper Stop
125 Lower Diaphragm Housing Vents
130 Receiver Vents
135 Fill Valve
140 Valve Housing
145 Valve Seat
150 Check Ball
155 Valve Spring
160 Working Gas
165 Enclosed Container Power Supply
170 Movable Surface
175 Movable Surface Area
180 Enclosed Container Unloaded Volume
185 Reset Head
190 Reset Pusher Head
195 Reset Handles
200 Enclosed Container Loaded Volume
205 Latch Mechanism
210 Bolt Holes
215 Trigger Spring
220 Receiver Recess
225 Safety Link
230 Safety Link Lock
235 Trigger Key
240 Trigger Button
241 Safety Link Tab
242 Snap Ring
243 Safety Link Spring
244 Safety Link Seat
245 Disposable Ampule
250 Ampule Head
255 Ampule Housing
260 Ampule Cylinder
265 Ampule Cylinder Head
270 Ampule Piston
275 Ampule Piston Head
280 Ampule Volume
285 Piston Active Seal
290 Orifice
295 Conical Orifice Entrance
300 Security Seal
305 Sterility Cover
310 Ampule Outer Body
315 Enclosed Container Length
320 Adjunct Container
325 Stroke Length
327 Lower Diaphragm Housing Side Vents
330 Connecting Port
335 Enclosed Container Power Supply
340 Bellows
345 Upper Bellows End
350 Lower Bellows End
355 Corrugated Side Wall
360 Upper Bellows Housing End Plate
365 Ram Plate
370 Enclosed Container
372 Enclosed Container Inside Space
373 Enclosed Container Outside Space
375 Enclosed Container Loaded Volume
380 Enclosed Container Unloaded Volume
385 Bellows Housing
390 Weld
395 Lower Bellows Housing End Plate
400 Weld
405 Bellows Housing Vent
410 Bumper Stop
415 Receiver
420 Receiver Head
425 Ram
430 Latch Groove
435 Ram Head
440 Latching Ball Holes
445 Latching Balls
450 Retainer
455 Retainer Recess
460 Latch Spring
465 Snap Ring
470 Retainer Slot
475 Trigger Pin
480 Trigger
485 Trigger Cap
490 Access Hole
500 Trigger Spring
505 Safety Link
510 Safety Link Pivot
515 Enclosed Container Power Supply
520 Movable Surface
525 Latch Mechanism
530 Movable Surface Area
535 Enclosed Container Length
537 Stroke Length
540 Retainer Slot Lower Edge
545 Safety Spring
550 Reset Housing
555 Reset Levers
560 Reset Handle Pivots
565 Reset Handle Stops
575 Reset Housing Slots
580 Reset Pushing Latches
585 Reset Pushing Latch Pivots
590 Reset Pushing Latch Stops
595 Reset Holding Latches
600 Reset Holding Latch Pivots
605 Reset Pusher
610 Ratchet Pushing Sets
612 Ratchet Holding Sets
615 Reset Pusher Bushings
617 Reset Pusher Slide
619 Top Reset Pusher Stop
620 Bottom Reset Pusher Stop
625 Holding Latch Springs
630 Holding Latch Spring Stops
635 Reset Lever Springs
640 Reset Lever Spring Pivots
645 Pushing Latch Springs 650 Pushing Latch Spring Pivots
655 Reset Holding Latch Pivot Sites
660 Reset Lever Spring Pivot Sites
665 Reset Handle Pivot Sites
670 Holding Latch Spring Stop Sites
675 Reset Pushing Latch Stop Sites
678 Handle Relief
680 Two-Stage Enclosed Container Needleless Injector
685 Enclosed Container Loaded Volume
690 Intermediate Diaphragm Ring
695 Diaphragm Means
700 Intermediate Diaphragm Stop
701 First Stage Movable Surface
702 Inner Diaphragm Section
703 Outer Diaphragm Section
705 First Stage Movable Surface Area
710 Lower Diaphragm Housing Ring Stop
715 Lower Diaphragm Housing Ring
720 Enclosed Container Intermediate Volume
723 Lower Diaphragm Housing
725 Lower Diaphragm Housing Outer Vent
727 Second Stage Movable Surface
728 Second Stage Movable Surface Area
733 Enclosed Container Unloaded Volume
735 Lower Diaphragm Housing Inner Vent
737 Enclosed Container
738 Enclosed Container Power Supply
739 Ampule Intermediate Volume
740 Enclosed Container Loaded Volume
745 Bellows Housing
750 First Bellows
755 Intermediate Connector Plate
760 Second Bellows
765 Intermediate Connector Tube
770 Intermediate Connector Vent
773 First Stage Movable Surface
775 First Stage Movable Surface Area
780 Bellows Housing Intermediate Stop
785 Enclosed Container Intermediate Volume
790 Second Stage Movable Surface Area
793 Second Stage Movable Surface
795 Enclosed Container Unloaded Volume
800 Enclosed Container
805 Enclosed Container Power Supply Various modifications can be made to the present invention without departing from the apparent scope hereof.

We claim:

1. A power supply to be used in a drug delivery device for rapidly delivering a drug, said power supply comprising;
   A. an enclosed container with an inside space containing a compressed gas and an enclosed container surface that separates said inside space from an outside space at a pressure lower than the compressed gas, said enclosed container providing for an expansion of said compressed gas from a first smaller volume to a second larger volume,
   B. said enclosed container having a portion of said enclosed container surface comprising a movable surface with a movable surface area that undergoes a movement during the expansion of said compressed gas,
   C. said enclosed container surface having a continuous surface without having an active seal between said inside space and the outside space,
   D. said movable surface able to be interfaced with a means for containing the drug to cause the drug to be delivered rapidly from the means for containing the drug during the expansion of said compressed gas.

2. The power supply of claim 1 wherein said enclosed container comprises a diaphragm.

3. The power supply of claim 1 wherein said enclosed container comprises a bellows.

4. The power supply of claim 1 wherein the drug delivery device is a needleless injector.

5. A power supply to be used in a drug delivery device for rapidly delivering a drug, said power supply comprising;
   A. an enclosed container with an inside space containing a compressed gas and an enclosed container surface that separates said inside space from an outside space at a pressure lower than the compressed gas, said enclosed container providing for an expansion of said compressed gas from a first smaller volume to a second larger volume,
   B. said enclosed container having a portion of said enclosed container surface comprising a movable surface with a movable surface area that undergoes a movement during the expansion of said compressed gas,
   C. said enclosed container surface having a continuous surface without having an active seal between said inside space and the outside space,
   D. said movable surface able to be interfaced with a device latching means for holding said enclosed container in said first smaller volume,
   E. said movable surface able to be interfaced with a reservoir means for containing the drug to cause the drug to be delivered rapidly from the reservoir means during the expansion of said compressed gas to said second larger volume upon release of the device latching means.

6. The power supply of claim 5 wherein said enclosed container comprises a diaphragm.

7. The power supply of claim 5 wherein said enclosed container comprises a bellows.

8. The power supply of claim 5 wherein the drug delivery device is a needleless injector.

9. A power supply to be used in a drug delivery device for rapidly delivering a drug, said power supply comprising;
   A. an enclosed container with an inside space containing a compressed gas and an enclosed container surface that separates said inside space from an outside space at a pressure lower than the compressed gas, said enclosed container providing for an expansion of said compressed gas from a first smaller volume to a second larger volume and providing for a compression of said compressed gas from said second larger volume to said first smaller volume,
   B. said enclosed container having a portion of said enclosed container surface comprising a movable surface with a movable surface area that undergoes a movement during the expansion of said compressed gas and a movement during the compression of said compressed gas,
   C. said enclosed container surface having a continuous surface without having an active seal between said inside space and the outside space,
   D. said movable surface able to be interfaced with a device latching means for holding said enclosed container in said first smaller volume,
   E. said movable surface able to be interfaced with a reservoir means for containing the drug to cause the drug to be delivered rapidly from the reservoir means during the expansion of said compressed gas upon release of the device latching means, F. said movable surface able to be interfaced with a reset for compressing said compressed gas from said second larger volume to said first smaller volume.

10. The power supply of claim 9 wherein said enclosed container comprises a diaphragm.

11. The power supply of claim 9 wherein said enclosed container comprises a bellows.

12. The power supply of claim 9 further comprising an adjunct container connected to said enclosed container and in fluid communication therewith.

13. The power supply of claim 9 wherein said enclosed container has a fill valve.

14. The power supply of claim 13 wherein said fill valve provides a site for adding additional compressed gas or removing compressed gas from said enclosed container.

15. The power supply of claim 14 wherein said fill valve allows said compressed gas to be added in order to increase a spring rate or a spring constant for said enclosed container.

16. The power supply of claim 14 wherein said fill valve allows said compressed gas to be added in order to increase pressure provided by said compressed gas.

17. The power supply of claim 9 wherein said compressed gas is a gas taken from a group including nitrogen, air, carbon dioxide, argon, and oxygen.

18. The power supply of claim 9 wherein said movable surface area can be increased to increase the spring rate and spring constant for said enclosed container.

19. The power supply of claim 9 wherein said second larger volume of said enclosed container is increased by a percentage while maintaining said movable surface area approximately constant to cause a drop in spring rate for the enclosed container.

20. The power supply of claim 9 wherein the drug delivery device is a needleless injector.

21. A power supply to be used in a drug delivery device for rapidly delivering a drug, said power supply comprising;
   A. an enclosed container with an inside space containing a compressed gas and an enclosed container surface that separates said inside space from an outside space, said enclosed container providing for an expansion of said compressed gas from a first smaller volume to a second larger volume and providing for a compression of said compressed gas from said second larger volume to said first smaller volume,
   B. said enclosed container having a portion of said enclosed container surface comprising a plurality of movable surfaces with a plurality of movable surface areas that undergoes a movement during the expansion of said compressed gas and a movement during the compression of said compressed gas,
   C. said enclosed container surface having a continuous surface without having an active seal between said inside space and the outside space,
   D. at least one movable surface of said plurality of movable surfaces able to be interfaced with a device latching means for holding said enclosed container in said first smaller volume,
   E. at least one movable surface of said plurality of movable surfaces able to be interfaced with a reservoir means for containing the drug to cause the drug to be delivered rapidly from the reservoir means during the expansion of said compressed gas upon release of the device latching means,
   F. at least one movable surface of said plurality of movable surfaces able to be interfaced with a reset means for compressing said compressed gas from said second larger volume to said first smaller volume, wherein said plurality of movable surfaces provides for a step change in movement rate of at least one of said plurality of movable surfaces during the expansion of said compressed gas.

22. The power supply of claim 21 wherein said enclosed container comprises a plurality of diaphragm sections.

23. The power supply of claim 21 wherein said plurality of movable surfaces comprises a plurality of diaphragm sections.

24. The power supply of claim 21 wherein said enclosed container comprises a plurality of bellows.

25. The power supply of claim 21 further comprising an adjunct container connected to said enclosed container and in fluid communication therewith.

26. The power supply of claim 21 wherein the drug delivery device is a needleless injector.

27. A power supply to be used in a drug delivery device for rapidly delivering a drug, said power supply comprising;
   A. An enclosed container with an inside space containing a working gas that can be compressed to store potential energy and can be expanded to release the stored potential energy and an enclosed container surface that separates said inside space from an outside space, said enclosed container providing for an expansion of said working gas from a first smaller volume to a second larger volume and providing for a compression of said working gas from said second larger volume to said first smaller volume,
   B. said enclosed container having a portion of said enclosed container surface comprising a first movable surface and a second movable surface each with a different movable surface area which undergo a movement during the expansion of said working gas and a movement during the compression of said working gas,
   C. said enclosed container surface having a continuous surface without having an active seal between said inside space and the outside space,
   D. said first and second movable surfaces able to be interfaced with a device latching means for holding said enclosed container in said first smaller volume,
   E. said first and second movable surfaces able to be interfaced with a reservoir means for containing the drug to cause the drug to be delivered rapidly from the reservoir means during the expansion of said working gas upon release of the device latching means,
   F. said first and second movable surfaces able to be interfaced with a reset means for compressing said working gas from said second larger volume to said first smaller volume.

28. The power supply of claim 27 wherein said first movable surface has a first movable surface area and said second movable surface has a second movable surface area, said first movable surface area being larger than said second movable surface area.

29. The power supply of claim 28 wherein said first movable surface is able to be interfaced with the reservoir means to apply a larger force than a stepped change to a smaller force applied to the reservoir means through interface with said second movable surface during the expansion of said working gas.

30. The power supply of claim 28 wherein said first movable surface comprises a first diaphragm section and a second diaphragm section and said second movable surface comprises said second diaphragm section.

31. The power supply of claim 27 wherein said enclosed container comprises two diaphragm sections.

32. The power supply of claim 27 wherein said enclosed container comprises two bellows.

33. The power supply of claim 27 wherein the drug delivery device is a needleless injector.

34. The method of use of a power supply for a drug delivery device for rapidly delivering a drug comprising the steps;
- A. providing a power supply having an enclosed container with an inside space containing a compressed gas, said inside space being in fluid communication with itself, said enclosed container having a surface that separates said inside space from an outside space not in fluid communication with said inside space, the outside space having a pressure that is lower than the compressed gas, said enclosed container providing for an expansion of said compressed gas from a first smaller volume to a second larger volume,
- B. said enclosed container having a portion of said surface which is a movable surface with a movement during the expansion of said compressed gas,
- C. said enclosed container having a continuous surface without having an active seal between said inside space and said outside space,
- D. holding said movable surface of said enclosed container in said first smaller volume using a latching means of a drug delivery device,
- E. expanding said compressed gas from said first smaller volume to said second larger volume upon release of the latching means.

35. The method of claim 34 wherein the drug delivery device is a needleless injector.

36. The method of resetting a power supply for a drug delivery device for rapidly delivering a drug comprising the steps;
- A. providing a power supply having an enclosed container with an inside space containing a compressed gas, said inside space being in fluid communication with itself, said enclosed container having a surface that separates said inside space from an outside space not in fluid communication with said inside space, said enclosed container providing for an expansion of said compressed gas from a first smaller volume to a second larger volume and providing for a compression of said compressed gas from said second larger volume to said first smaller volume,
- B. said enclosed container having a portion of said surface which is a movable surface with a movement during the expansion of said compressed gas and a movement during the compression of said compressed gas,
- C. said enclosed container having a continuous surface without having an active seal between said inside space and said outside space,
- D. interfacing said movable surface with a reset means which compresses said compressed gas from said second larger volume to said first smaller volume,
- E. interfacing said movable surface of said enclosed container in said first smaller volume with a latch means of a drug delivery device to hold said movable surface.

37. The method of claim 36 wherein the drug delivery device is a needleless injector.

38. The method of use of a power supply for a drug delivery device for rapidly delivering a drug comprising the steps;
- A. providing a power supply having an enclosed container with an inside space containing a compressed gas, said inside space being in fluid communication with itself, said enclosed container having a surface that separates said inside space from an outside space not in fluid communication with said inside space, said enclosed container providing for an expansion of said compressed gas from a first smaller volume to a second larger volume and providing for a compression of said compressed gas from said second larger volume to said first smaller volume,
- B. said enclosed container having a portion of said surface which is a movable surface with a movement during the expansion of said compressed gas and a movement during the compression of said compressed gas,
- C. said enclosed container having a continuous surface without having an active seal between said inside space and said outside space,
- D. interfacing said movable surface of said enclosed container in said first smaller volume with a latch means of a drug delivery device to hold said movable surface,
- E. expanding said compressed gas from said first smaller volume to said second larger volume upon release of the latch means whereby said movable surface is interfaced with a drug reservoir means to cause drug to be delivered,
- F. interfacing said movable surface with a reset means which compresses said compressed gas from said second larger volume to said first smaller volume.

39. The method of claim 38 wherein the drug delivery device is a needleless injector.

* * * * *